(12) United States Patent
Viola et al.

(10) Patent No.: US 8,511,533 B2
(45) Date of Patent: *Aug. 20, 2013

(54) ANNULAR ADHESIVE STRUCTURE

(75) Inventors: Frank J. Viola, Sandy Hook, CT (US); Christopher J. Criscuolo, Branford, CT (US); David Fowler, Cheshire, CT (US); Michael J. Bettuchi, Middletown, CT (US); Danyel J. Tarinelli, Middletown, CT (US); Robert Capella, Shelton, CT (US); Kevin Sniffin, Danbury, CT (US); Ahmad R. Hadba, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 278 days.

This patent is subject to a terminal disclaimer.

(21) Appl. No.: 12/914,507

(22) Filed: Oct. 28, 2010

(65) Prior Publication Data
US 2011/0042442 A1    Feb. 24, 2011

Related U.S. Application Data

(63) Continuation of application No. 11/388,620, filed on Mar. 24, 2006, now Pat. No. 7,845,536, which is a continuation-in-part of application No. 11/248,846, filed on Oct. 12, 2005, now Pat. No. 7,823,592.

(60) Provisional application No. 60/620,268, filed on Oct. 18, 2004, provisional application No. 60/620,269, filed on Oct. 18, 2004, provisional application No. 60/620,066, filed on Oct. 18, 2004, provisional application No. 60/620,140, filed on Oct. 18, 2004, provisional application No. 60/669,104, filed on Apr. 7, 2005.

(51) Int. Cl.
*A61B 17/04* (2006.01)

(52) U.S. Cl.
USPC .................. 227/179.1; 227/178.1; 227/180.1

(58) Field of Classification Search
USPC ............... 227/178.1, 179.1, 180.1; 606/153, 606/219
See application file for complete search history.

(56) References Cited

U.S. PATENT DOCUMENTS

| | | |
|---|---|---|
| 3,054,406 A | 9/1962 | Usher |
| 3,124,136 A | 3/1964 | Usher |

(Continued)

FOREIGN PATENT DOCUMENTS

| | | |
|---|---|---|
| DE | 1 99 24 311 A1 | 11/2000 |
| DE | 199 24 311 A1 | 11/2000 |

(Continued)

OTHER PUBLICATIONS

International Search Report corresponding to European Application No. EP 10 25 0715.9, completed on Jun. 30, 2010 and mailed on Jul. 20, 2010; 3 pages.

(Continued)

*Primary Examiner* — Alexandra Elve
*Assistant Examiner* — Nathaniel Chukwurah

(57) ABSTRACT

An assembly for joining tissue is provided and includes an anvil assembly and a body portion juxtaposed with respect to one another along a shaft and arranged so as to be approximated with respect to one another; and an applicator supported on the anvil assembly and configured for retaining a wound treatment material therein and for dispensing the wound treatment material therefrom. A method for joining tissue is provided and includes the steps of dispensing the wound treatment material from the applicator so as to distribute wound treatment material onto at least one of a first tissue section and a second tissue section; and approximating the anvil assembly and the body portion to one another so that the first tissue section and the second tissue section are in contact with one another with the dispensed wound treatment material interposed therebetween.

16 Claims, 23 Drawing Sheets

(56) References Cited

U.S. PATENT DOCUMENTS

| | | |
|---|---|---|
| 4,347,847 A | 9/1982 | Usher |
| 4,354,628 A | 10/1982 | Green |
| 4,452,245 A | 6/1984 | Usher |
| 4,605,730 A | 8/1986 | Shalaby et al. |
| 4,655,221 A | 4/1987 | Devereux |
| 4,834,090 A | 5/1989 | Moore |
| 4,838,884 A | 6/1989 | Dumican et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze et al. |
| 5,205,459 A | 4/1993 | Brinkerhoff et al. |
| 5,222,963 A | 6/1993 | Brinkerhoff et al. |
| 5,238,026 A | 8/1993 | Goto |
| 5,263,629 A | 11/1993 | Trumbull et al. |
| 5,314,471 A | 5/1994 | Brauker et al. |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov et al. |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,165,185 A | 12/2000 | Shennib et al. |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,325 B1 | 10/2002 | Delmotte et al. |
| 6,461,368 B2 | 10/2002 | Fogarty et al. |
| 6,503,257 B2 | 1/2003 | Grant et al. |
| 6,503,259 B2 | 1/2003 | Huxel et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,927,315 B1 | 8/2005 | Heinecke et al. |
| 7,128,748 B2 | 10/2006 | Mooradian et al. |
| 7,147,138 B2 | 12/2006 | Shelton, IV |
| 7,431,730 B2 | 10/2008 | Viola |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,604,151 B2 | 10/2009 | Hess et al. |
| 7,665,646 B2 | 2/2010 | Prommersberger |
| 7,744,627 B2 | 6/2010 | Orban, III et al. |
| 7,793,813 B2 | 9/2010 | Bettuchi |
| 7,823,592 B2 | 11/2010 | Bettuchi et al. |
| 7,845,533 B2 | 12/2010 | Marczyk et al. |
| 7,845,536 B2 | 12/2010 | Viola et al. |
| 7,909,224 B2 | 3/2011 | Prommersberger |
| 2002/0016626 A1 | 2/2002 | DiMatteo et al. |
| 2002/0019187 A1 | 2/2002 | Carroll et al. |
| 2002/0052622 A1 | 5/2002 | Rousseau |
| 2002/0091397 A1 | 7/2002 | Chen |
| 2002/0133236 A1 | 9/2002 | Rousseau |
| 2002/0138152 A1 | 9/2002 | Francis et al. |
| 2002/0151911 A1 | 10/2002 | Gabbay |
| 2002/0165559 A1 | 11/2002 | Grant et al. |
| 2002/0165562 A1 | 11/2002 | Grant et al. |
| 2002/0165563 A1 | 11/2002 | Grant et al. |
| 2002/0177859 A1 | 11/2002 | Monassevitch et al. |
| 2003/0065345 A1 | 4/2003 | Weadock |
| 2003/0065346 A1 | 4/2003 | Evens et al. |
| 2003/0083676 A1 | 5/2003 | Wallace |
| 2003/0088256 A1 | 5/2003 | Conston et al. |
| 2003/0105510 A1 | 6/2003 | DiMatteo et al. |
| 2003/0114866 A1 | 6/2003 | Ulmsten et al. |
| 2003/0120284 A1 | 6/2003 | Palacios |
| 2003/0167064 A1 | 9/2003 | Whayne |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0034377 A1 | 2/2004 | Sharkawy et al. |
| 2004/0092960 A1 | 5/2004 | Abrams et al. |
| 2004/0093029 A1 | 5/2004 | Zubik et al. |
| 2004/0107006 A1 | 6/2004 | Francis et al. |
| 2004/0116945 A1 | 6/2004 | Sharkawy et al. |
| 2004/0142621 A1 | 7/2004 | Carroll et al. |
| 2004/0172048 A1 | 9/2004 | Browning |
| 2004/0209059 A1 | 10/2004 | Foss |
| 2004/0215214 A1 | 10/2004 | Crews et al. |
| 2004/0215219 A1 | 10/2004 | Eldridge et al. |
| 2004/0215221 A1 | 10/2004 | Suyker et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021026 A1 | 1/2005 | Baily |
| 2005/0021053 A1 | 1/2005 | Heinrich |
| 2005/0021085 A1 | 1/2005 | Abrams et al. |
| 2005/0025325 A1 | 2/2005 | Fischer |
| 2005/0059996 A1 | 3/2005 | Bauman et al. |

| | | |
|---|---|---|
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0145671 A1 | 7/2005 | Viola |
| 2005/0184121 A1 | 8/2005 | Heinrich |
| 2005/0228446 A1 | 10/2005 | Mooradian et al. |
| 2005/0230453 A1 | 10/2005 | Viola |
| 2005/0245965 A1 | 11/2005 | Orban et al. |
| 2006/0004407 A1 | 1/2006 | Hiles et al. |
| 2006/0025813 A1 | 2/2006 | Shelton et al. |
| 2006/0085034 A1 | 4/2006 | Bettuchi |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0212050 A1 | 9/2006 | D'Agostino et al. |
| 2006/0271104 A1 | 11/2006 | Viola et al. |
| 2007/0034669 A1 | 2/2007 | de la Torre et al. |
| 2007/0049953 A2 | 3/2007 | Shimoji et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, Iii et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |

FOREIGN PATENT DOCUMENTS

| | | |
|---|---|---|
| EP | 0 594 148 | 4/1994 |
| EP | 0 594 148 A1 | 4/1994 |
| EP | 0 327 022 B1 | 4/1995 |
| EP | 0 667 119 A1 | 8/1995 |
| EP | 1 064 883 A1 | 1/2001 |
| EP | 1 256 317 A2 | 11/2002 |
| EP | 1 306 061 A2 | 5/2003 |
| EP | 1 520 525 | 4/2005 |
| EP | 1 520 525 A1 | 4/2005 |
| EP | 1 621 141 | 2/2006 |
| EP | 1 759 640 A2 | 3/2007 |
| EP | 2 005 894 A2 | 12/2008 |
| EP | 2 005 895 A2 | 12/2008 |
| JP | 06327683 A | 11/1994 |
| WO | WO 90/05489 | 5/1990 |
| WO | WO 90/05489 A1 | 5/1990 |
| WO | WO 97/01989 A1 | 1/1997 |
| WO | WO 97/13463 | 4/1997 |
| WO | WO 98/17180 | 4/1998 |
| WO | WO 98/17180 A1 | 4/1998 |
| WO | WO 99/45849 | 9/1999 |
| WO | WO 99/45849 A1 | 9/1999 |
| WO | WO 03/082126 A1 | 10/2003 |
| WO | WO 03094746 A1 | 11/2003 |
| WO | WO 03/105698 A2 | 12/2003 |
| WO | WO 03/0206698 A2 | 12/2003 |
| WO | WO 2006/023578 | 3/2006 |
| WO | WO 2006/023578 A2 | 3/2006 |
| WO | WO 2006/044490 | 4/2006 |
| WO | WO 2006/044490 A2 | 4/2006 |
| WO | WO 2006/083748 A1 | 8/2006 |
| WO | WO 2008/057281 A2 | 5/2008 |
| WO | WO 2008/109125 A1 | 9/2008 |

OTHER PUBLICATIONS

International Search Report corresponding to European Application No. EP 10 25 0642.5, completed on Mar. 25, 2011 and mailed on Apr. 4, 2011; 4 pages.

International Search Report for PCT/US05/35120 date of completion is May 6, 2008 (10 pages).

European Search Report for EP 05803193.1-2310 date of completion is Feb. 9, 2010 (3 pages).

International Search Report for EP 08 25 1779 dated Jul. 23, 2008.

International Search Report for EP 06016962.0 dated Jan. 3, 2007.

International Search Report for PCT/US05/36740 date of completion is Mar. 23, 2007 (2 pages).

International Search Report for PCT/US2008/002981 dated Jun. 26, 2008.

International Search Report for EP 06016962.0 dated Mar. 23, 2007.

European Search Report for corresponding EP05 80 4382, date of completion is Oct. 5, 2010 (3 pages).

International Search Report corresponding to European Application No. EP 06 00 4598, completed on Jun. 22, 2006; 2 pages.

International Search Report corresponding to European Application No. EP 06 01 6962.0, completed on Jan. 3, 2007 and mailed on Jan. 11, 2007; 10 pages.

International Search Report corresponding to International Application No. PCT/US05/36740, completed on Feb. 20, 2007 and mailed on Mar. 23, 2007; 8 pages.

International Search Report corresponding to International Application No. PCT/US2008/002981, completed on Jun. 9, 2008 and mailed on Jun. 26, 2008; 2 pages.

International Search Report corresponding to European Application No. EP 08 25 1779, completed on Jul. 14, 2008 and mailed on Jul. 23, 2008; 5 pages.

International Search Report corresponding to European Application No. EP 08 25 1989.3, completed on Mar. 11, 2010 and mailed on Mar. 24, 2010; 3 pages.

International Search Report corresponding to European Application No. EP 10 25 1437.9, completed on Nov. 22, 2010 and mailed on Dec. 16, 2010; 3 pages.

International Search Report corresponding to European Application No. EP 09 25 2897.5, completed on Feb. 7, 2011 and mailed on Feb. 15, 2011; 3 pages.

European Search Report for EP 12150511.9.3-2310 date of completion is Apr. 16, 2012 (7 pages).

European Search Report for EP 11164908.3-2310 date of completion is Jan. 5, 2012 (7 pages).

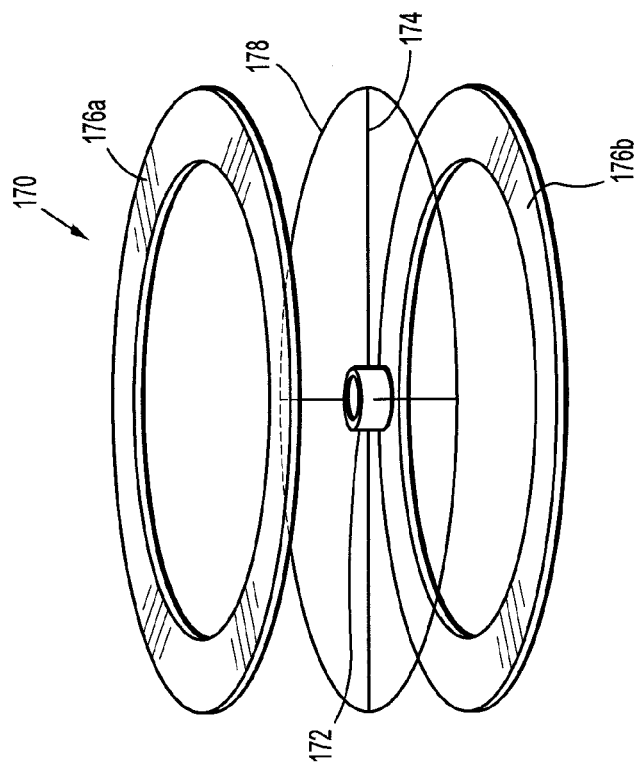
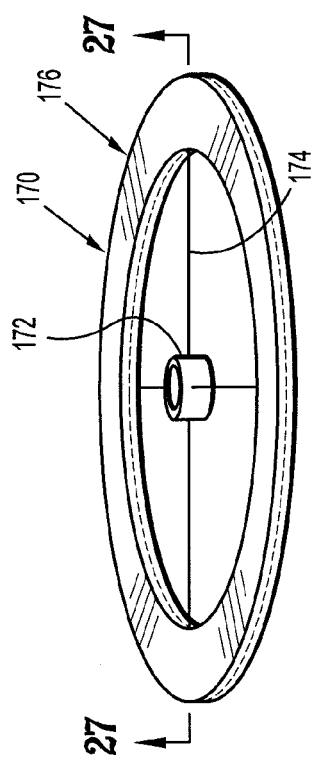
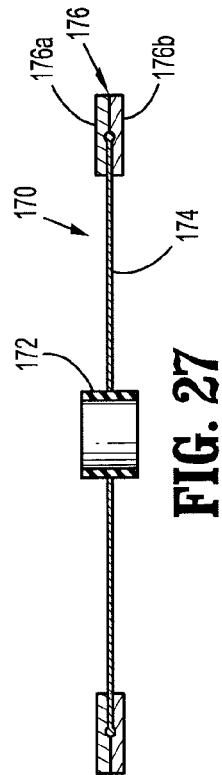
FIG. 28
FIG. 26
FIG. 27

ANNULAR ADHESIVE STRUCTURE

CROSS-REFERENCE TO RELATED APPLICATIONS

This application is a continuation of U.S. application Ser. No. 11/388,620 filed Mar. 24, 2006 now U.S. Pat. No. 7,845,536, which is a continuation in part of U.S. application Ser. No. 11/248,846 filed Oct. 12, 2005, now patented U.S. Pat. No. 7,823,592, which claims benefit of each of U.S. Provisional Application No. 60/620,268 filed Oct. 18, 2004, U.S. Provisional Application No. 60/620,269 filed Oct. 18, 2004, U.S. Provisional Application No. 60/620,066 filed Oct. 18, 2004, U.S. Provisional Application No. 60/620,140 filed Oct. 18, 2004 and U.S. Provisional Application No. 60/669,104 filed Apr. 7, 2005 and the disclosures of each of the above-identified applications are hereby incorporated by reference in their entirety.

BACKGROUND

1. Technical Field

The present disclosure relates to devices and methods for applying compositions including wound treatment materials, adhesives and/or sealing compositions, for use with or without stapling devices, for joining tissue, and for reducing occurrences of leaking, bleeding and/or stricture.

2. Background of Related Art

Throughout the years the medical field has utilized various techniques in an effort to join or bond body tissue together. Historically, suturing was the accepted technique for rejoining severed tissues and closing wounds. Suturing was achieved with a surgical needle and a suturing thread, and more recently, with a variety of polymeric or metallic staples, as will be discussed below. The intended function of sutures is to hold the edges of a wound or tissue against one another during the healing process so as to reduce discomfort, pain, scarring and the time required for healing.

Recently, many procedures which in the past required conventional suturing have been replaced by staple suturing which involves the application of the staples to the edges of the wound or tissue with the use of a surgical stapler. Surgical staplers have been developed for joining adjacent tissue, for providing hemostasis of adjacent tissue and for providing hemostasis in conjunction with cutting of adjacent tissue. Such surgical staplers include both linear and annular type configurations. A typical linear stapler and cutter includes parallel rows of staples with a slot for a cutting means to travel between the rows of staples.

Staples have traditionally been used to replace suturing when joining or anastomosing various body structures, such as, for example, the bowel or bronchus. The surgical stapling devices employed to apply these staples are generally designed to simultaneously cut and join an extended segment of tissue in a patient, thus vastly reducing the time and risks of such procedures.

Linear or annular surgical stapling devices are employed by surgeons to sequentially or simultaneously apply one or more rows of surgical fasteners, e.g., staples or two-part fasteners, to body tissue for the purpose of joining segments of body tissue together and/or for the creation of anastomoses. Linear surgical stapling devices generally include a pair of jaws or finger-like structures between which body tissue to be joined is placed. When the surgical stapling device is actuated and/or "fired", firing bars move longitudinally and contact staple drive members in one of the jaws, and surgical staples are pushed through the body tissue and into/against an anvil in the opposite jaw thereby crimping the staples closed. A knife blade may be provided to cut between the rows/lines of staples. Examples of such surgical stapling devices are described in U.S. Pat. Nos. 4,354,628, 5,014,899 and 5,040,715, the entirety of each of which is incorporated herein by reference.

Annular surgical stapling devices generally include an annular staple cartridge assembly including a plurality of annular rows of staples, typically two, an anvil assembly operatively associated with the annular cartridge assembly, and an annular blade disposed internal of the rows of staples. Examples of such annular surgical stapling devices are described in U.S. Pat. Nos. 5,799,857 and 5,915,616 to Robertson et al., the entirety of each of which is incorporated herein by reference.

For most procedures, the use of bare staples, with the staples in direct contact with the patient's tissue, is generally acceptable. The integrity of the tissue will normally serve to prevent the staples from tearing out of the tissue and compromising the sealing before healing has occurred. However, in some surgical operations, surgical supports, e.g., meshes, are employed by surgeons to bridge, repair and/or reinforce tissue defects with a patient, especially those occurring in the abdominal wall, chest wall, diaphragm and other musculo-aponeurotic areas of the body. Examples of surgical supports are disclosed in U.S. Pat. Nos. 3,054,406, 3,124,136, 4,347,847, 4,655,221, 4,838,884 and 5,002,551, the entirety of each of which is incorporated herein by reference.

When the staples are applied in surgical procedures utilizing surgical meshes, supports, buttresses and the like (i.e., reinforcing material), the legs of the staple typically pass from the cartridge jaw through a layer of the surgical support, and through the patient's tissue before encountering the anvil jaw. In an alternative procedure, the legs of the staple typically pass from the cartridge jaw through a first layer of the surgical support, then through the patient's tissue, and finally through a second layer of the surgical support before encountering the anvil jaw. With the staples in place, the stapled tissue is clamped between the layers of the surgical support. Reference may be made to U.S. Pat. No. 5,542,594, the entire content of which is incorporated herein by reference, for a more detailed discussion of the use of surgical supports in cooperation with surgical stapling instrument.

In addition to the use of surgical staples, biological tissue adhesives have been developed for joining tissue. Generally, biological adhesives bond separated tissues together. Such adhesives may be used instead of suturing and stapling, for example, in surgical procedures, for the repair of tissue or the creation of anastomoses.

In addition to the use of biological adhesives, following the formation of the anastomosis, a separate instrument or device is used to apply biological sealants to the outer surface of the anastomosis. Typically, in a separate step, the biological sealants are applied to the outer surface of the anastomosis. The biological sealants are intended to reduce and/or stop the incidents of leakage from the anastomosis.

One possible side effect of any end-to-end bowel anastomosis is its tendency to stenos over time, which stenosis can decrease the diameter of the lumen over time. Accordingly, the need exists for a surgical support structure which operates in conjunction with any end-to-end anastomosis device and assists in maintaining the lumen of the anastomosed bowel or other tubular organ open over time.

The application of suitable biocompatible adhesive offers many advantages to the patient and the surgeon alike, such as, for example, the possible reduction in the number of staples used, immediate sealing of the tissue being treated, a strengthening of the anastomosis, and a reduction in the occurrence of bleeding from the blood vessels, leakage through the tissue joint, and stricture. Moreover, use of biocompatible adhesives tends to minimize foreign body reaction and scarring.

There is a need for surgical stapling instruments and devices, which reduce the trauma suffered by a patient, reduce the number of gaps between or at individual staple sites, reduce leakage of fluids, reduce bleeding, and/or which create a relatively strong bond between adjacent body tissues, e.g., along staple lines and tissue seams.

Accordingly, the need exists for devices for applying structures and compositions which operate with or without surgical staples to assist in maintaining the joined tissue, including maintaining the tubular organs patent or open over time.

A need also exists for structures which operate with or without surgical staples to reduce the trauma suffered by the patient, reduce the instances of leakage, reduce the instances of bleeding, and create a relatively strong bond between adjacent body tissues.

SUMMARY

The present disclosure relates to devices and methods for applying wound treatment materials for use with or without stapling devices, for joining tissue, and for reducing occurrences of leaking, bleeding and/or stricture.

According to an aspect of the present disclosure, an assembly for joining tissue is provided and includes an anvil assembly and a body portion juxtaposed with respect to one another along a shaft and arranged so as to be approximated with respect to one another; and an applicator supported on the anvil assembly and configured for retaining a wound treatment material therein and for dispensing the wound treatment material therefrom.

The applicator may include a sleeve operatively connected to the anvil assembly, wherein the wound treatment material is retained within and dispensed from the sleeve. The applicator may further include an ampoule selectively positionable within the sleeve, wherein the wound treatment material is retained within and dispensed from the ampoule. The applicator may still further include a manifold supported on the anvil assembly, wherein the manifold defines at least one channel therein for directing a flow of wound treatment material. The manifold may be supported on the shaft.

Each channel of the manifold may be in fluid communication with the sleeve and the ampoule. The manifold may extend radially outward from the shaft and wherein each channel formed therein is radially oriented.

The applicator may include a seal interposed between the sleeve and the ampoule. The applicator and the shaft may be complementarily configured for bayonet-type coupling therebetween.

The body portion may carry a plurality of surgical staples in an annular configuration. The surgical staples may be deployable against the anvil. The assembly may further include an annular knife disposed radially inwardly of the staples.

According to another aspect of the present disclosure, a method of joining tissue is provided. The method includes the steps of providing an apparatus having an anvil assembly including a stem; an applicator supported on the stem of the anvil assembly and configured for retaining a wound treatment material therein and for dispensing the wound treatment material therefrom; and a body portion in juxtaposition to the anvil assembly and arranged so as to be approximated with respect to the anvil assembly.

The method further includes the steps of dispensing the wound treatment material from the applicator so as to distribute wound treatment material onto at least one of a first tissue section and a second tissue section; and approximating the anvil assembly and the body portion to one another so that the first tissue section and the second tissue section are in contact with one another with the dispensed wound treatment material interposed therebetween.

The wound treatment material may be at least one of an adhesive, a sealant, a hemostat, and a medicament.

The applicator may include a sleeve operatively connected to the anvil assembly; an ampoule selectively positionable within the sleeve, wherein the wound treatment material is retained within and dispensed from the ampoule; and a manifold supported on the anvil assembly, wherein the manifold defines at least one channel therein for directing a flow of wound treatment material. The method may further include the step of dispensing the wound treatment material from the ampoule and out through each channel.

The manifold may extend radially outward from the stem of the anvil assembly and each channel formed therein may be radially oriented. The applicator may include a seal interposed between the sleeve and the ampoule.

The method may further include the step of dispensing the wound treatment material in a radially outward direction. The method may include the step of dispensing the wound treatment material from at least one channel of the manifold. The method may further include the step of dispensing the wound treatment material from the ampoule and out through at least one channel of the manifold.

The body portion may include a connection member. Accordingly, the applicator and the connection member may be complementarily configured for bayonet-type coupling therebetween.

The body portion may carry a plurality of surgical staples in an annular configuration wherein the surgical staples are deployable against the anvil assembly. The method may further include the step of stapling the first tissue section to the second tissue section.

The apparatus may further include an annular knife disposed radially inwardly of the staples. Accordingly, the method may further include the step of severing the first and second tissue sections at a location radially inward of the staples.

BRIEF DESCRIPTION OF DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure, wherein:

FIG. 26 is a perspective view of a support structure for use with the assembly of FIGS. 22-25;

FIG. 27 is a cross-sectional view of the support structure of FIG. 26, as taken through 27-27 of FIG. 26;

FIG. 28 is an exploded perspective view of the support structure of FIGS. 26 and 27;

DETAILED DESCRIPTION OF EMBODIMENTS

Figure 1:
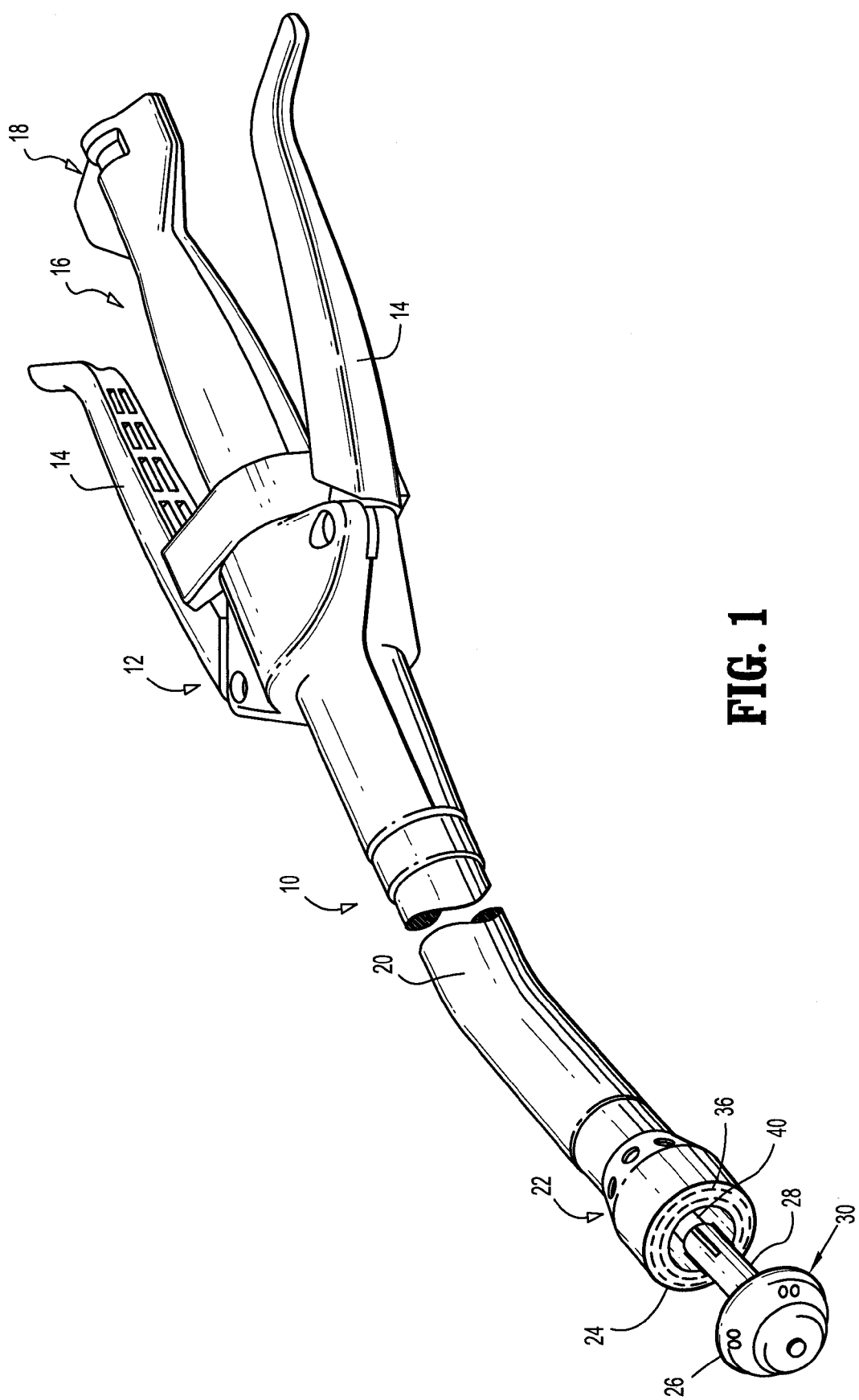
FIG. 1 is a perspective view of an exemplary annular surgical stapling device.

Embodiments of the presently disclosed devices and structures will now be described in detail with reference to the drawing figures wherein like reference numerals identify similar or identical elements. As used herein and as is traditional, the term "distal" refers to that portion which is furthest from the user while the term "proximal" refers to that portion which is closest to the user.

Referring initially to FIG. 1, an annular surgical stapling device, for use with the annular adhesive structures disclosed herein, is generally designated as 10. Surgical stapling device 10 includes a handle assembly 12 having at least one pivotable actuating handle member 14, and an advancing member 16. Extending from handle member 12, there is provided a tubular body portion 20 which may be constructed so as to have a curved shape along its length. Body portion 20 terminates in a staple cartridge assembly 22 which includes one or more arrays of staple receiving slots 36 having a staple (not shown) disposed in each one of staple receiving slots 36. Typically, a pair of annular arrays of staple receiving slots 36 is provided. Positioned distally of staple cartridge assembly 22 there is provided an anvil assembly 30 including an anvil member 26 and a shaft 28 operatively associated therewith for removably connecting anvil assembly 30 to a distal end portion or connection member 40 of stapling device 10.

Staple cartridge assembly 22 may be fixedly connected to the distal end of tubular body portion 20 or may be configured to concentrically fit within the distal end of tubular body portion 20. Typically, staple cartridge assembly 22 includes a staple pusher (not shown) including a proximal portion having a generally frusto-conical shape and a distal portion defining two concentric rings of peripherally spaced fingers (not shown), each one of which is received within a respective staple receiving slot 36.

Typically, a knife (not shown), substantially in the form of an open cup with the rim thereof defining a knife edge, is disposed within staple cartridge assembly 22 and mounted to a distal surface of the staple pusher (not shown). The knife edge is disposed radially inward of the pair of annular arrays of staples. Accordingly, in use, as the staple pusher is advanced, the knife is also advanced axially outward.

Reference may be made to U.S. Pat. No. 5,915,616 to Viola et al., the entire content of which is incorporated herein by reference, for a detailed discussion of annular stapling device 10. Although a circular stapling apparatus is shown in FIG. 1, the stapling device may be arranged to deploy staples in a semi-circular or other desired shape. Although discussed with reference to intestinal tissue, devices according to the present disclosure can be arranged to join and/or treat other tissues in other procedures.

Figure 2:
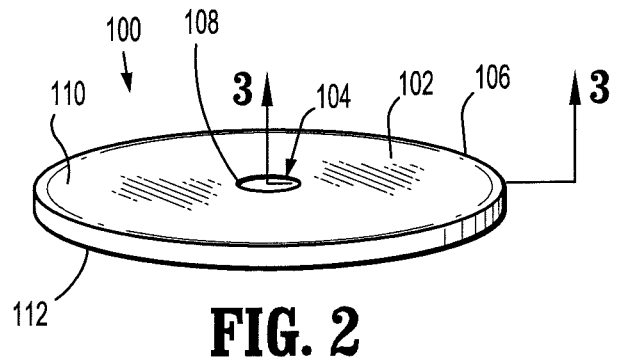
FIG. 2 is a perspective view of a support structure in accordance with an embodiment of the present disclosure, for use with the annular surgical stapling device of FIG. 1.

Turning now to FIG. 2, an adhesive or support structure, in accordance with an embodiment of the present disclosure, is generally designated as 100. Structure 100 desirably has a shape corresponding to the arrays of staple receiving slots 36. Preferably, the structure 100 includes a washer-like or disk-like body portion 102 including a substantially centrally located aperture 104 formed therethrough. Structure 100 is defined by an outer terminal edge 106, an inner terminal edge 108 defining the size of aperture 104, an upper surface 110, and a bottom surface 112.

In one embodiment, structure 100 is sized such that when structure 100 is operatively associated with stapling device 10, as will be described in greater detail below, outer terminal edge 106 extends radially beyond staple retaining pockets 36 of staple cartridge assembly 22. Additionally, aperture 104 of structure 100 is sized to at least receive shaft 28 of anvil assembly 30 therethrough. In another embodiment, the distance between outer terminal edge 106 and inner terminal edge 108 is substantially equal to a width of a tissue contact surface 24 (see FIG. 1) of staple cartridge assembly 22.

It is contemplated that body portion 102 of structure 100 may be fabricated from or include a surgical grade, biocompatible, non-absorbable (i.e., permanent) material; desirably a mesh impregnated with an adhesive, sealant and/or wound treatment material. For example, body portion 102 may be fabricated from "TEFLON", which is a registered trademark owned by DuPont de Nemours & Co. It is further contemplated that body portion 102 may be fabricated from a biocompatible polymeric foam, felt, polytetrafluoroethylene (ePTFE), gelatin, fabric or the like, or any other biocompatible material.

Non-absorbable materials used for body portion 102 include, and are not limited to, those that are fabricated from such polymers as polyethylene, polypropylene, nylon, polyethylene terephthalate, polytetrafluoroethylene, polyvinylidene fluoride, and the like. Further non-absorbable materials include and are not limited to stainless steel, titanium and the like.

In one embodiment, body portion 102 of structure 100 may be fabricated from a bio-absorbable material which is desirably impregnated with an adhesive, sealant, and/or other wound treatment material (e.g., a medicament). Accordingly, a sealant component of structure 100 can be used to retard any bleeding which may occur from the tissue, an adhesive component of structure 100 can be used to secure the approximated tissue together, and the bio-absorbability of structure 100 allows for structure 100 to be absorbed into the body after a predetermined amount of time. For example, structure 100 may remain in place in the body for approximately 2-3 weeks in order for the anastomosis to sufficiently heal prior to structure 100 being absorbed into the body. In other embodiments, the structure 100 has at least one portion that is absorbable and at least one portion that is not absorbable.

Bio-absorbable materials used for body portion 102 of structure 100 include, and are not limited to, those fabricated from homopolymers, copolymers or blends obtained from one or more monomers selected from the group consisting of glycolide, glycolic acid, lactide, lactic acid, p-dioxanone, α-caprolactone and trimethylene carbonate. Other bio-absorbable materials include and are not limited to, for example, Polyglycolic Acid (PGA) and Polylactic Acid (PLA). In one embodiment, body portion 102 may be fabricated from bio-absorbable felt, ePTFE, gelatin or any other bio-absorbable materials.

It is contemplated that the adhesive is a biocompatible adhesive including, but not limited to, adhesives which cure upon tissue contact, which cure upon exposure to ultraviolet (UV) light, which are two-part systems which are kept isolated from one another and cure upon coming into contact with one another, which are pressure sensitive, which are any combinations thereof, or any other known suitable adhesive. In one embodiment, it is contemplated that an adhesive having a cure time of from about 10 to 15 seconds may be used. In another embodiment, it is contemplated that an adhesive having a cure time of about 30 seconds may be used.

It is envisioned that body portion 102 of structure 100 may be impregnated with a pre-cured adhesive or sealant. The pre-cured sealant or adhesive will react with the moisture and/or heat of the body tissue to thereby activate the sealing and/or adhesive properties of the sealant or adhesive. It is envisioned that the pre-cured sealant or adhesive may be a hydro-gel or the like.

It is envisioned that the wound treatment material "W" includes and is not limited to one or a combination of adhesives, hemostats, sealants, coagulants, astringents, and medicaments. Other surgically biocompatible wound treatment materials "W" which may be employed in or applied by surgical instruments, including surgical staplers, include adhesives whose function is to attach or hold organs, tissues or structures; sealants to prevent fluid leakage; hemostats to halt or prevent bleeding; coagulants, astringents (e.g., sulfates of aluminum) and medicaments. Examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively. Examples of sealants, which can be employed, include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc. Examples of hemostat materials, which can be employed, include fibrin-based, collagen-based, oxidized regenerated cellulose-based and gelatin-based topical hemostats. Examples of commercially available hemostat materials are fibrinogen-thrombin combination materials sold under the trade designations CoStasis™ by Tyco Healthcare Group, LP, and Tisseel™ sold by Baxter International, Inc.

The wound treatment material may include a cross-linking material and/or reactive agent that reacts with the support structure, tissue or both. The resulting material acts as a seal or tissue joining material that is non-absorbable. For example, the wound treatment material may be based on biocompatible cross-linked polymers formed from water soluble precursors having electrophilic and nucleophilic groups capable of reacting and cross-linking in situ, including those disclosed in U.S. Pat. No. 6,566,406, the entire contents of which are incorporated herein by reference.

The wound treatment material may be disposed on structure 100 or impregnated into structure 100. Medicaments may include one or more medically and/or surgically useful substances such as drugs, enzymes, growth factors, peptides, proteins, dyes, diagnostic agents or hemostasis agents, monoclonal antibodies, or any other pharmaceutical used in the prevention of stenosis.

Wound treatment material "W" may include visco-elastic film forming materials, cross-linking reactive agents, and energy curable adhesives. It is envisioned that wound treatment material "W", and in particular, adhesive may be cured with the application of water and/or glycerin (e.g., 1,2,3-pranatetriol, also known as glycerol and glycerine) thereto. In this manner, the water and/or glycerin cure the adhesive and hydrate the wound.

In one embodiment, it is contemplated that body portion 102 of structure 100 may be impregnated with a first component of a two-part adhesive and that the device deploys the second component of the two-part adhesive. For example, in a surgical stapler 10, the staples, which are retained in staple receiving slots 36 of staple cartridge assembly 22, are coated with a second component (e.g., a reactant) of the two-part adhesive. In this manner, the first component of the adhesive is activated when the staples penetrate and capture body portion 102 of structure 100 during the firing sequence of surgical stapling device 10, and the two components of the adhesive contact one another.

As seen in FIG. 2, structure 100 may include a single layered body portion 102 including a homogeneous array of bio-absorbable or non-absorbable materials or a heterogeneous array of bio-absorbable and/or non-absorbable materials. In certain embodiments, body portion 102 is impregnated with a pressure sensitive adhesive which is activated when adjacent layers of tissue are approximated, with the body portion 102 disposed therebetween.

Figure 3:
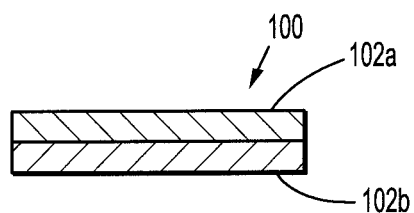
FIG. 3 is a cross-sectional view of a support structure in accordance with an alternate embodiment of the present disclosure, as taken through 3-3 of FIG. 2, for use with the annular surgical stapling device of FIG. 1.
Figure 4:
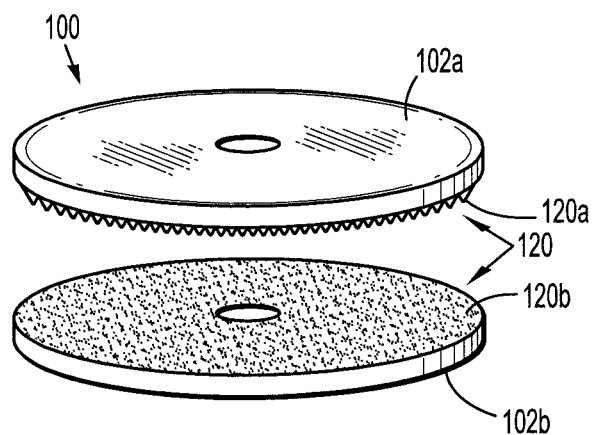
FIG. 4 is a perspective view of a support structure in accordance with another embodiment of the present disclosure, for use with the annular surgical stapling device of FIG. 1.

In an alternate embodiment, as seen in FIGS. 3 and 4, structure 100 may include a layered body portion having at least two layers as indicated by first layer, film or wafer 102a and second layer, film or wafer 102b. In this embodiment, each layer 102a, 102b may include a homogeneous or heterogeneous array of bio-absorbable and/or non-absorbable materials. It is envisioned that each layer 102a, 102b may be separated from one another, as seen in FIG. 4, prior to the surgical procedure.

As will be described in greater detail below, first layer 102a of structure 100 is placed against a surface of a first tissue to be anastomosed, in juxtaposition to a second tissue to be anastomosed, and second layer 102b of structure 100 is placed against a surface of the second tissue to be anastomosed, in juxtaposition to the first tissue to be anastomosed. In this manner, as the first and second tissues are brought into contact with one another first and second layers 102a, 102b of structure 100 are brought into contact with one another and allowed to mix and/or react. For example, first layer 102a of structure 100 includes a first component of a two-part adhesive or sealant while second layer 102b of structure 100 includes a second component of the two-part adhesive or sealant. Accordingly, in use, when first layer 102a and second layer 102b come into contact with one another, the first and second components of the two-part adhesive or sealant will also come into contact and mix to thereby form the adhesive or sealant.

First and second layers 102a, 102b may be fabricated as bio-absorbable film-like membranes which activate upon contact with one another and/or contact with a fluid (e.g., water, saline, blood, an activating fluid, etc.). It is envisioned that a break-way or tear-away divider or barrier (not shown) may be positioned between first and second layers 102a, 102b in order to prevent accidental and/or premature contact between first and second layers 102a, 102b. It is further envisioned that each first and second layer 102a, 102b may include a liner (not shown) removably disposed on at least one of a top and bottom surface thereof. In any of these embodiments, prior to contact of first and second layers 102a, 102b with one another, the divider and/or liners must be removed in order for activation of the adhesive to occur.

It is further contemplated that the structure may be in the form of an absorbable gel pack filled with adhesive. For example, the structure may be a tubular ring, similar to annular adhesive structure 200 as will be described in greater detail below.

In accordance with an embodiment of the present disclosure, as seen in FIG. 4, it is envisioned that each layer 102a, 102b of structure 100 includes one portion of a hook and loop type fastener 120 (e.g., Velcro™). For example, first layer 102a includes a hook portion 120a of hook and loop type fastener 120 disposed on a surface thereof, and second layer 102b includes a loop portion 120b of the hoop and loop type fastener 120 disposed on a surface thereof. Accordingly, in use, first and second layers 102a, 102b are secured to one another via the hook and loop type fastener so as to provide more time for the two components of the two-part adhesive or sealant to react with one another. Desirably, the hook and loop type fastener are fabricated from bio-absorbable materials.

Figure 5:
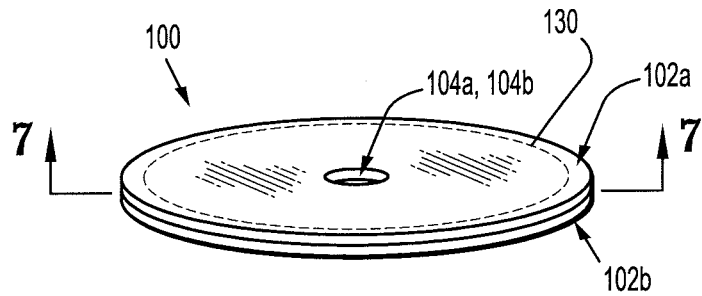
FIG. 5 is a perspective view of a support structure in accordance with yet another embodiment of the present disclosure, for use with the annular surgical stapling device of FIG. 1.
Figure 6:
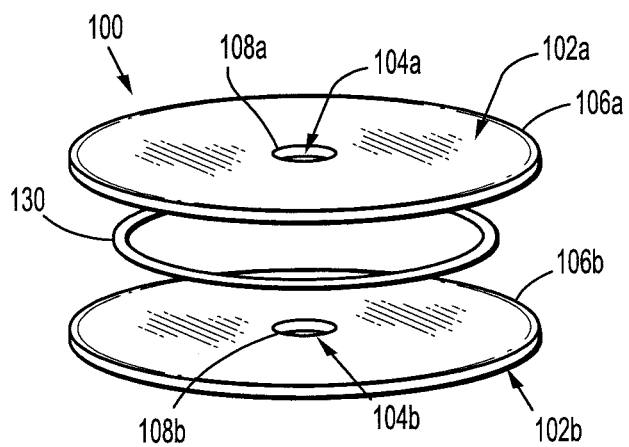
FIG. 6 is an exploded perspective view of the support structure of FIG. 5.
Figure 7:
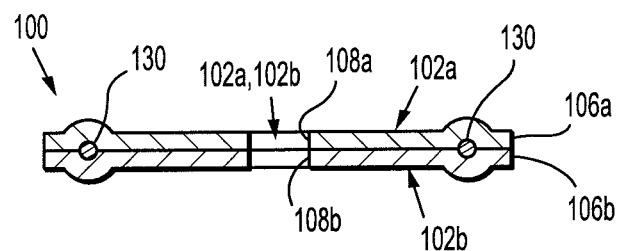
FIG. 7 is a cross-sectional view of the support structure of FIGS. 5 and 6, as taken through 7-7 of FIG. 5.

As seen in FIGS. 5-7, each of first and second layers 102a, 102b of structure 100 includes an outer terminal edge 106a, 106b, respectively, and an inner terminal edge 108a, 108b respectively, defining a substantially centrally located aperture 104a, 104b, formed therethrough. Apertures 104a and 104b are axially aligned with one another and are sized to permit positioning of shaft 28 of anvil assembly 30 therethrough.

First and second layers 102a, 102b are sized such that when structure 100 is in an expanded condition, outer terminal edges 106a, 106b of first and second layers 102a, 102b extend radially beyond staple receiving slots 36 of staple cartridge assembly 22. First and second layers 102a, 102b may be fabricated from two laminated pieces of pliable material, such as, for example, ePTFE.

Structure 100 further includes a ring, hoop or other circular member 130 secured or disposed between first layer 102a and second layer 102b. Hoop 130 may be made from a resilient material, or a shape memory wire (e.g., NITINOL) wherein hoop 130 has a ring-like memorized shape.

It is envisioned that a layer of a reinforcing mesh or the like (not shown) may be disposed between first and second layers 102a, 102b, or incorporated within the first layer 102a and/or second layer 102b. In this manner, the reinforcing mesh may provide structure 100 with increased strength and structural integrity to maintain the patency of the lumen between the anastomosed tissues.

The inner terminal edge 108a, 108b of structure 100 is operatively connected to shaft 28 of anvil assembly 30, and the structure 100 is collapsed with hoop 130 biased against shaft 28 to thereby provide a low profile during insertion of anvil assembly 30 into the target surgical site. The structure 100 may be maintained collapsed against the shaft 28 by a breakable sleeve or removable member. In use, the anvil assembly 30 is connected to connection member 40 of tubular body portion 20 of surgical stapling device 10. Following insertion of anvil assembly 28, including structure 100, into the target surgical site and to the distal end of tubular body portion 20 of surgical stapling device 10, hoop 130 is allowed to return to is memorized shape thereby expanding structure 100 such that outer terminal edges 106a, 106b of first and second layers 102a, 102b extend radially beyond staple receiving slots 36 of staple cartridge assembly 22. The breakable sleeve may be broken upon introduction of wound treatment material into the structure 100 or may be connected to an actuator at a proximal end of the device.

Since first and/or second layers 102a, 102b of structure 100 may be fabricated from a bio-absorbable material which is impregnated with a wound treatment material, such as an adhesive, a sealant, and/or a medicament, in use, the sealant component would function to retard any bleeding which may occur from the tissue, the adhesive component would function to secure the approximated tissue together, and the bio-absorbability of structure 100 allows for at least a portion of structure 100 to be absorbed into the body after a predetermined amount of time. It is envisioned that hoop 130 may be fabricated from a bio-absorbable material as well. In this manner, hoop 130 will ultimately be absorbed into the body. For example, in such an embodiment, structure 100 may be constructed such that first and second layers 102a, 102b remain in place in the body for approximately 2-3 weeks in order for the anastomosis to sufficiently heal while hoop 130 remains in place in the body for some time after that in order to help maintain the patency of the lumen.

Figure 8:
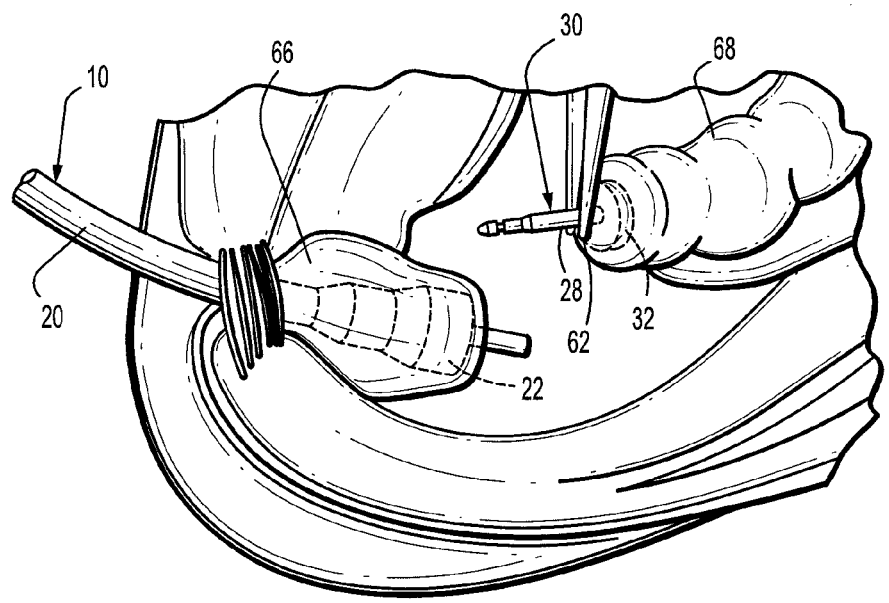
FIG. 8 is a perspective view of the intestinal area of a patient, illustrating a method of positioning any of the support structures of FIGS. 2-7 on the anvil rod of the annular stapling device of FIG. 1.

Turning now to FIG. 8, there is illustrated the use of surgical stapling device 10 and detachable anvil assembly 30 in an anastomosis procedure to effect joining of intestinal sections 66 and 68. The anastomosis procedure is typically performed using minimally invasive surgical techniques including laparoscopic means and instrumentation. At the point in the procedure shown in FIG. 8, a diseased intestinal section has been previously removed, anvil assembly 30 has been applied to the operative site either through a surgical incision or trans-anally and positioned within intestinal section 68, and tubular body portion 20 of surgical stapling device 10 has been inserted trans-anally into intestinal section 66. Intestinal sections 66 and 68 are also shown temporarily secured about their respective components (e.g., shaft 28 of anvil assembly 30, and the distal end of tubular body portion 20) by conventional means such as a purse string suture "P" (see FIG. 9).

Figure 9:
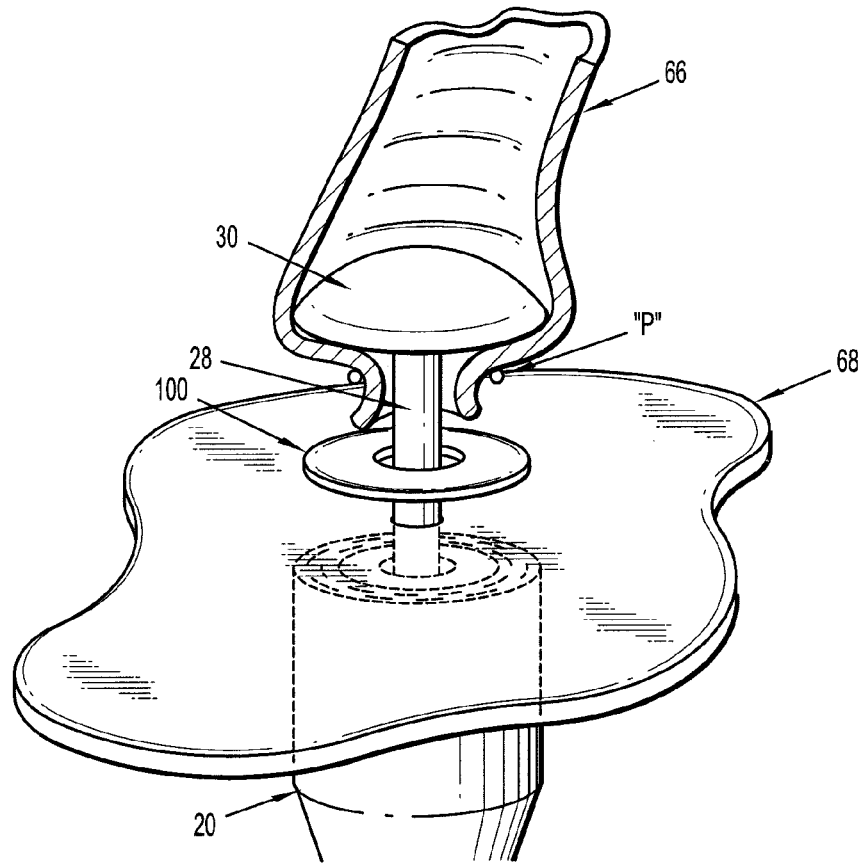
FIG. 9 is a schematic perspective view of the intestinal area of FIG. 8, illustrating the anvil rod mounted to the annular stapling device and having any of the support structure of FIGS. 2-7 disposed therebetween.

According to one method, as seen in FIG. 9, if desired or if the surgical procedure requires, structure 100 may be placed onto shaft 28 of anvil assembly 30 prior to the coupling of anvil assembly 30 to the distal end of tubular body portion 20. Following positioning of structure 100 onto shaft 28 of anvil assembly 30, the surgeon maneuvers anvil assembly 30 until the proximal end of shaft 28 is inserted into the distal end of tubular body portion 20 of surgical stapling device 10, wherein the mounting structure within the connection member 40 at the distal end of tubular body portion 20 engages shaft 28 to effect the mounting.

Thereafter, anvil assembly 30 and tubular body portion 20 are approximated using rotatable grip member 18 of handle member 12 to approximate intestinal sections 66, 68 and capture structure 100 therebetween. Surgical stapling device 10 is then fired by manipulating the handle member 12 thereby stapling intestinal sections 66, 68 to one another and cutting the portion of tissue and structure 100 disposed radially inward of the knife, to complete the anastomosis. Structure 100 may then release the adhesive impregnated therein to thereby adhere intestinal sections 66 and 68 to one another.

In the event that a structure 100, having a first and second layer 102a, 102b each including one part of a two-part adhesive composition, is used, it is envisioned that first and second layers 102a, 102b are maintained separated and/or isolated from one another until approximation and firing of surgical stapling device is to occur. Accordingly, in use, one of first and second layers 102a, 102b may be placed on shaft 28 of anvil assembly 30, against the surface of intestinal section 68, while the other of first and second layers 102a, 102b is placed against the surface of intestinal section 66. It is envisioned that pins (not shown) may extend distally from the distal end of tubular body portion 20 and penetrate through intestinal section 66. In this manner, the other of first and second layers 102a, 102b may be pinned onto the pins extending through intestinal section 66.

Alternatively, if a structure 100, having a first and second layer 102a, 102b each including one part of a two-part adhesive composition, is used, it is envisioned that that each layer 102a, 102b may be provided with a tear-away or removable liner for maintaining first and second layers 102a, 102b separated and/or isolated from one another. Accordingly, both first and second layers 102a, 102b may be placed on shaft 28 of anvil assembly 30.

If a structure 100, having a first and second layer 102a, 102b, each including one part of a two-part adhesive composition, is used, the adhesive composition is activated upon first and second layers 102a, 102b coming into contact with one another.

Turning now to FIGS. 10-15, in an embodiment of a support structure, support structure 100 includes at least one, preferably a pair of drapes, skirts or membranes 140, 142 (e.g., a first membrane 140 and a second membrane 142) extending from outer terminal edge 106 of body portion 102. Desirably, membranes 140, 142 are fabricated from a polymeric or plastic film including, and not limited to, polyethylene and the like. Each membrane 140, 142 includes a first or outer surface 140a, 142a, respectively, and a second or inner surface 140b, 142b, respectively.

Figure 10:
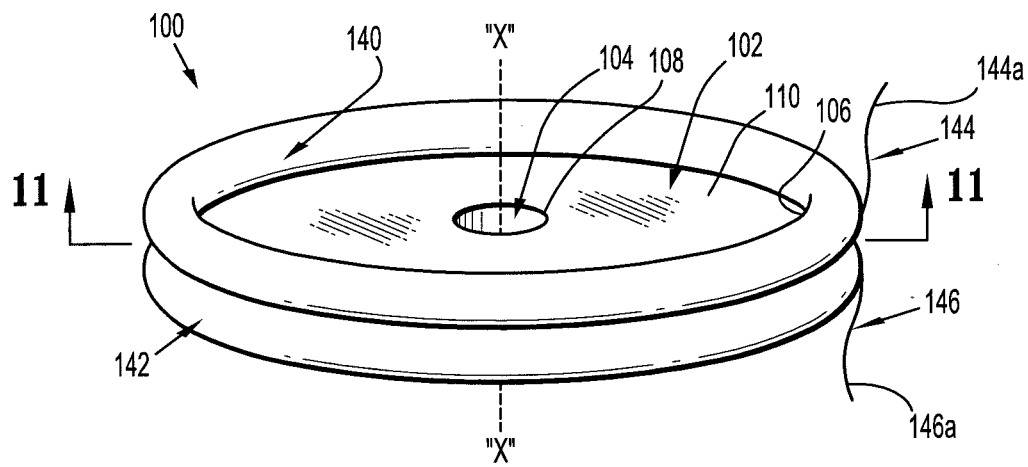
FIG. 10 is a perspective view of a support structure, according to another embodiment of the present disclosure, shown in an undeployed condition.
Figure 11:
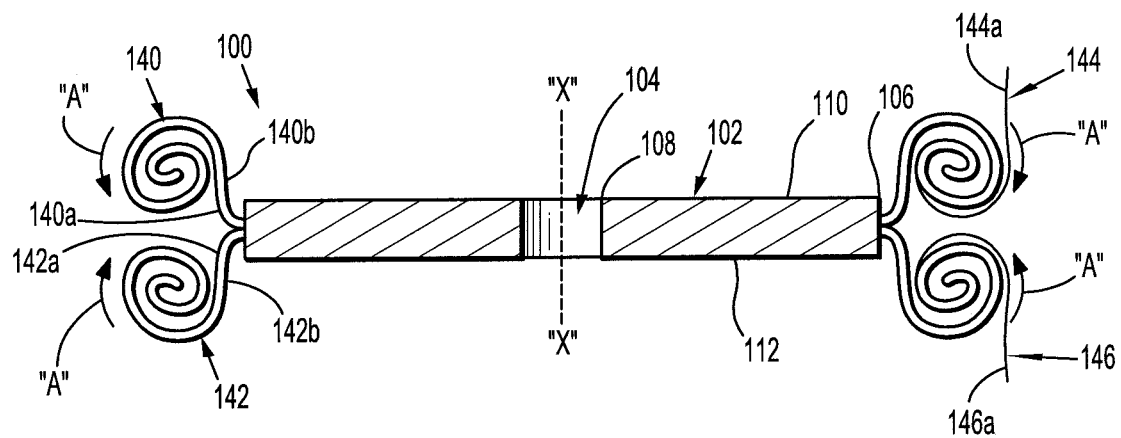
FIG. 11 is a cross-sectional view of the support structure of FIG. 10, as taken through 11-11 of FIG. 10.
Figure 12:
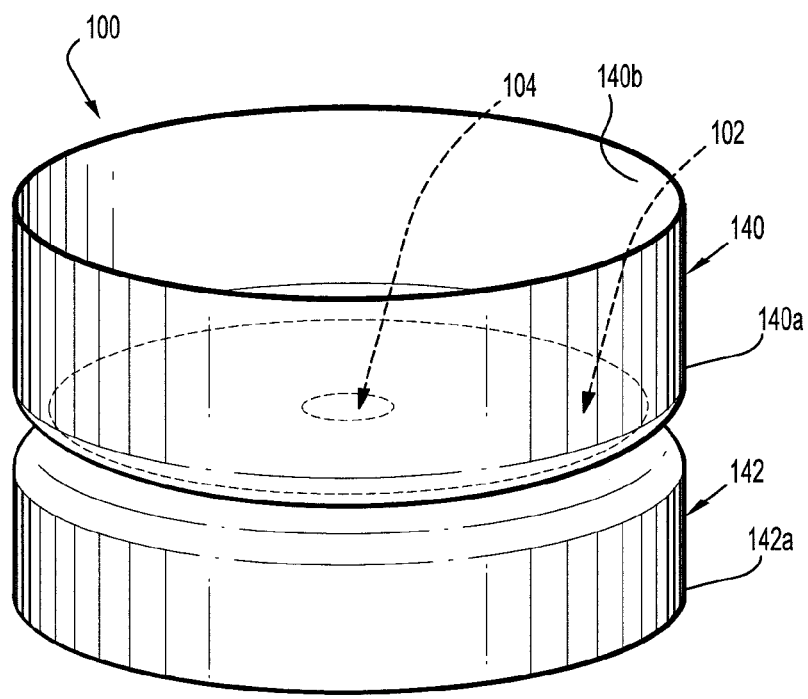
FIG. 12 is a perspective view of the support structure of FIGS. 10 and 11, shown in a deployed condition.
Figure 13:
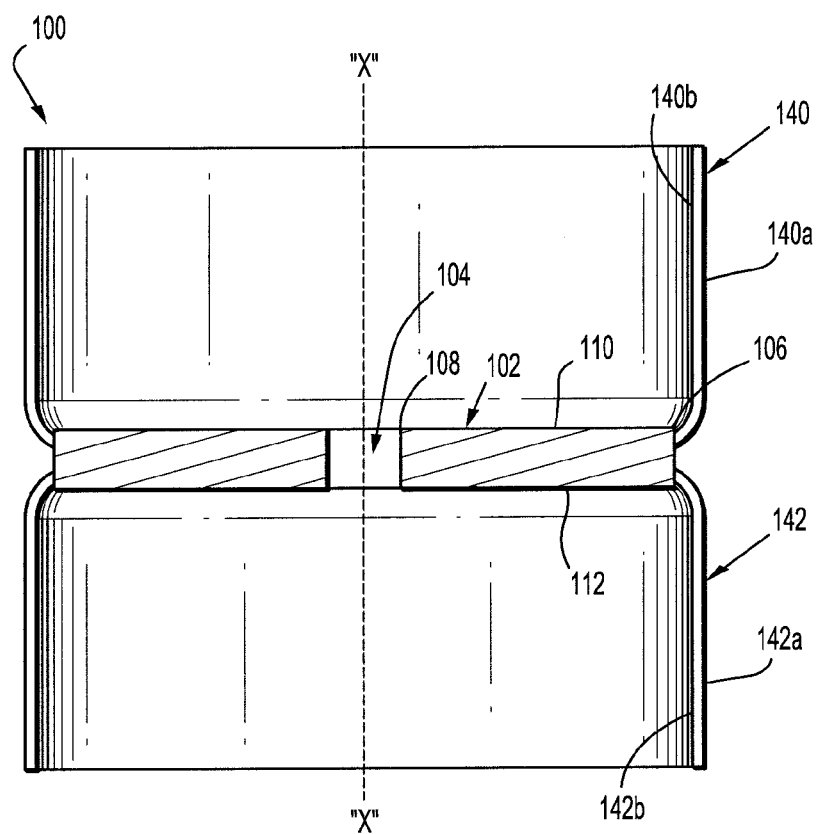
FIG. 13 is a cross-sectional view of the support structure of FIGS. 10-12.

As seen in FIGS. 10 and 11, membranes 140, 142 have a first, undeployed condition wherein membranes 140, 142 are rolled-up or others collapsed towards body portion 102. Desirably, membranes 140, 142 are rolled under in a direction toward the first or outer surfaces 140*a*, 142*a* thereof, as indicated by arrows "A" of FIG. 11. As seen in FIGS. 12 and 13, membranes 140, 142 have a second, deployed condition wherein membranes 140, 142 are unrolled or unfurled to extend in a substantially parallel orientation with respect to the central "X" axis. As will be described in greater detail below, first membrane 140 is unrolled in a first direction, preferably in a distal direction (e.g., in a direction extending away from upper surface 110 of body portion 102), and second membrane 142 is unrolled in a second direction, preferably in a proximal direction (e.g., in a direction extending away from lower surface 112 of body portion 102).

As seen in FIGS. 10 and 11, support structure 100 desirably includes one or more rip-cords or tethers 144, 146 rolled-up into membranes 140, 142. Rip-cords 144, 146 include free ends 144*a*, 146*a* which extend from membranes 140, 142 when membranes 140, 142 are in the rolled-up condition. In this manner, as will be described in greater detail below, as rip-cords 144, 146 are pulled, desirably in a distal direction and a proximal direction, membranes 140, 142 are un-rolled or un-furled accordingly.

In one embodiment, it is envisioned that body portion 102 of support structure 100 is formed of a foam material over-molded onto a relatively thin flexible material or film integral with membranes or sleeves 140, 142. Desirably, when un-rolled or un-furled, each membrane 140, 142 extends approximately 2.0 cm from body portion 102. In other words, when un-rolled or un-furled, first membrane 140 extends from body portion 102 by approximately 2.0 cm from upper surface 110 of body portion 102, and second membrane 142 extends from body portion 102 approximately 2.0 cm from lower surface 112 of body portion 102.

Figure 15:
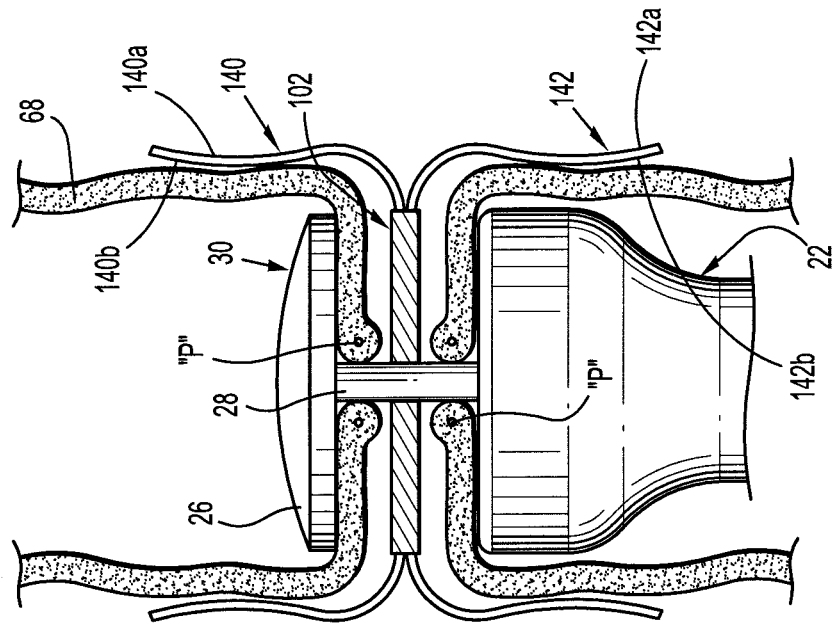
FIG. 15 is a longitudinal cross-sectional view illustrating the anvil rod mounted to the annular stapling device within a surgical site and the support structure of FIGS. 10-13, in a deployed condition, disposed between the apposed surfaces of the tissue.
Figure 14:
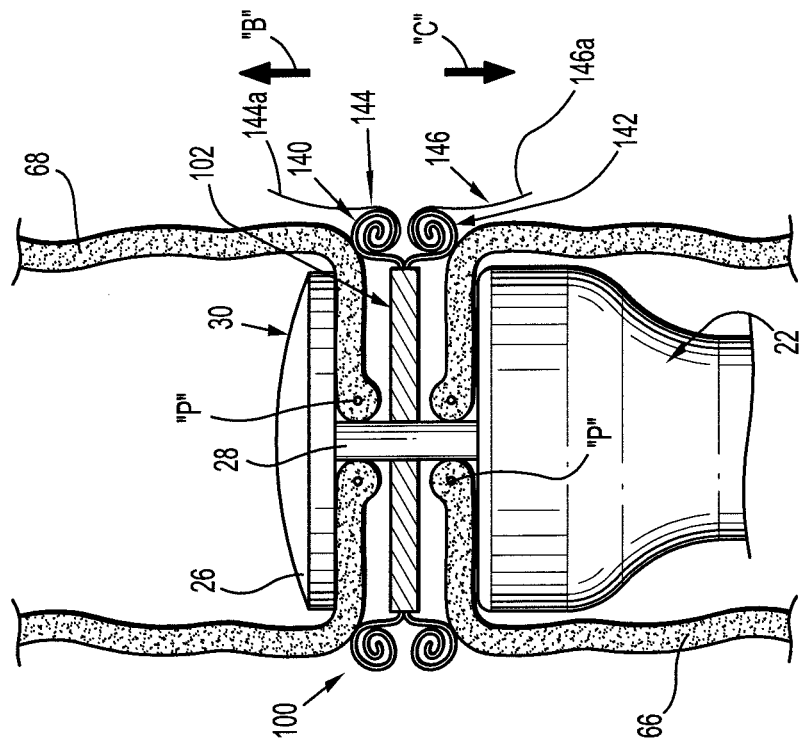
FIG. 14 is a longitudinal cross-sectional view illustrating the anvil rod mounted to the annular stapling device within a surgical site and the support structure of FIGS. 10-13, in an undeployed condition, disposed between the apposed surfaces of the tissue.
Figure 16:
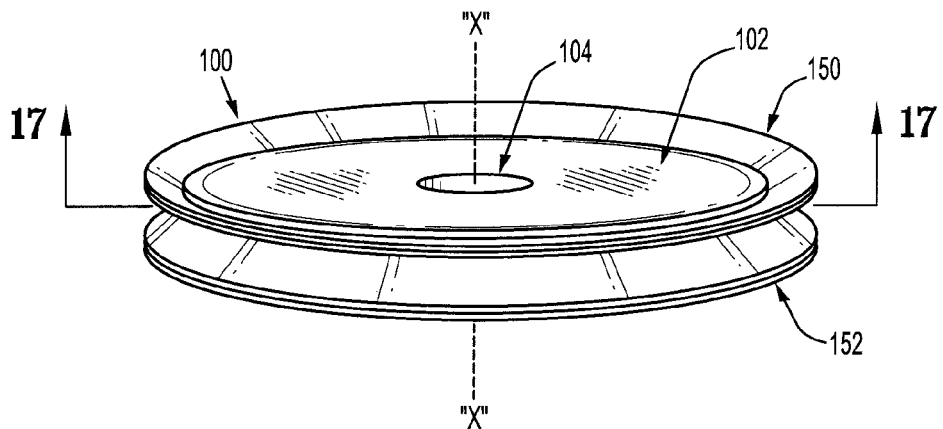
FIG. 16 is a perspective view of an support structure according to an alternate embodiment of the present disclosure.
Figure 17:
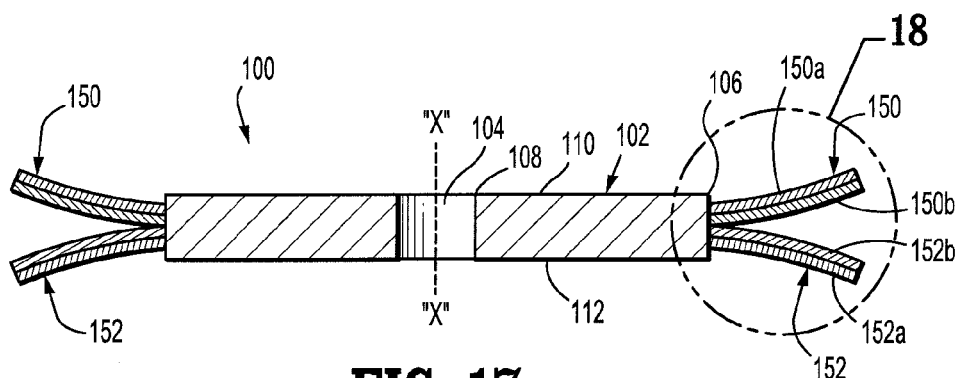
FIG. 17 is a cross-sectional view of the support structure of FIG. 16, as taken through 17-17 of FIG. 16.

Turning now to FIGS. 14 and 15, there is illustrated the use of surgical stapling device 10 and support structure 100 in an anastomosis procedure to effect joining of intestinal sections 66 and 68. The anastomosis procedure is typically performed using minimally invasive surgical techniques including laparoscopic means and instrumentation. At the point in the procedure shown in FIGS. 14 and 15, a diseased intestinal section has been previously removed, anvil assembly 30 has been introduced to the operative site either through a surgical incision or trans-anally and positioned within intestinal section 68, and tubular body portion 20 of surgical stapling device 10 has been inserted trans-anally into intestinal section 66. Intestinal sections 66 and 68 are also shown temporarily secured about their respective components (e.g., shaft 28 of anvil assembly 30, and the distal end of tubular body portion 20) by conventional means such as a purse string suture "P".

Support structure 100 is then placed onto shaft 28 of anvil assembly 30 prior to the coupling of anvil assembly 30 to the distal end of tubular body portion 20. In particular, shaft 28 of anvil assembly 30 is inserted into aperture 104 of body portion 102. Following positioning of structure 100 onto shaft 28 of anvil assembly 30, the surgeon maneuvers anvil assembly 30 until the proximal end of shaft 28 is inserted into the connection member 40 at the distal end of tubular body portion 20 of surgical stapling device 10, wherein the mounting structure (not shown) within the connection member 40 engages shaft 28 to effect the mounting.

Thereafter, as seen in FIG. 15, anvil assembly 30 and tubular body portion 20 are approximated to approximate intestinal sections 66, 68 and capture body portion 102 of structure 100 therebetween. With body portion 102 captured between intestinal sections 66, 68, as seen in FIG. 15, membranes 140, 142 are deployed (i.e., un-rolled or un-furled) as described above. In particular, first membrane 140 is un-rolled or un-furled in a distal direction, as indicated by arrow "B", so as to over-lie intestinal section 68, and second membrane 142 is un-rolled or un-furled in a proximal direction, as indicated by arrow "C", so as to over-lie intestinal section 66. Desirably, first and second membranes 140, 142 are un-rolled or un-furled by pulling on rip-cords 144, 146 in a distal or proximal direction, as necessary.

Membranes 140, 142 extend a predetermined distance over intestinal sections 66 and 68 (e.g., approximately 2 cm). When un-rolled or un-furled, membranes 140, 142 desirably adhere to the surface of intestinal sections 66, 68. The membranes may comprise a pressure-sensitive adhesive, or other adhesive material, incorporated with the membranes or coated thereon. Membranes 140 and 142 function to inhibit leakage from the anastomosis site and/or function to strengthen or reinforce intestinal sections 66, 68. With membranes 140, 142 deployed, as seen in FIG. 15, surgical stapling device 10 may be fired thereby stapling intestinal sections 66, 68 to one another and cutting the portion of tissue and structure 100 disposed radially inward of the knife, to complete the anastomosis.

Turning now to FIGS. 16-21, structure 100 includes at least one, preferably a pair of membranes 150, 152 (e.g., a first membrane 150 and a second membrane 152) extending from outer edge 106 of body portion 102. Each membrane 150 and 152 includes two layers, an inner layer 150*a*, 152*a*, respectively, and an outer layer 150*b*, 152*b*, respectively. Desirably, the materials selected for the construction of membranes 150, 152 swell at different rates when in the presence of moisture or fluid. In this manner, membranes 150, 152 will tend to bend or curl about the layer having the relatively slower rate of fluid swelling or fluid absorption. In this manner, support structure 100 has a first undeployed condition in which membranes 150, 152 extend substantially radially outward from body portion 102, and a second deployed condition in which membranes 150, 152 are substantially aligned with the central "X" axis of body portion 102.

In accordance with one embodiment, it is envisioned that inner layer 150*a*, 152*a* of membranes 150, 152 are constructed from a material that does not substantially absorb moisture or non-expanding (i.e., static) material, such as, for example, a bio-absorbable mesh fabricated from polyglycolic acid, sold under the tradename Dexon™, available from Tyco Healthcare Group LP, Norwalk, Conn. It is also envisioned that outer layer 150*b*, 152*b* of membranes 150, 152 are constructed from a moisture absorbing or expanding (i.e., dynamic) material, such as, for example, hydrogel and the like.

Desirably, each membrane 150 and 152 includes a hydrogel outer layer 150*b*, 152*b* laminated to a bio-absorbable mesh inner layer 150*a*, 152*a*. Furthermore, support structure 100 includes a foam body portion 102 laminated over the layered membrane 150, 152 materials. While each membrane 150, 152 desirably includes a pair of layers, it is envisioned and within the scope of the present disclosure for membranes 150, 152 to include any number of layers.

Figure 18:
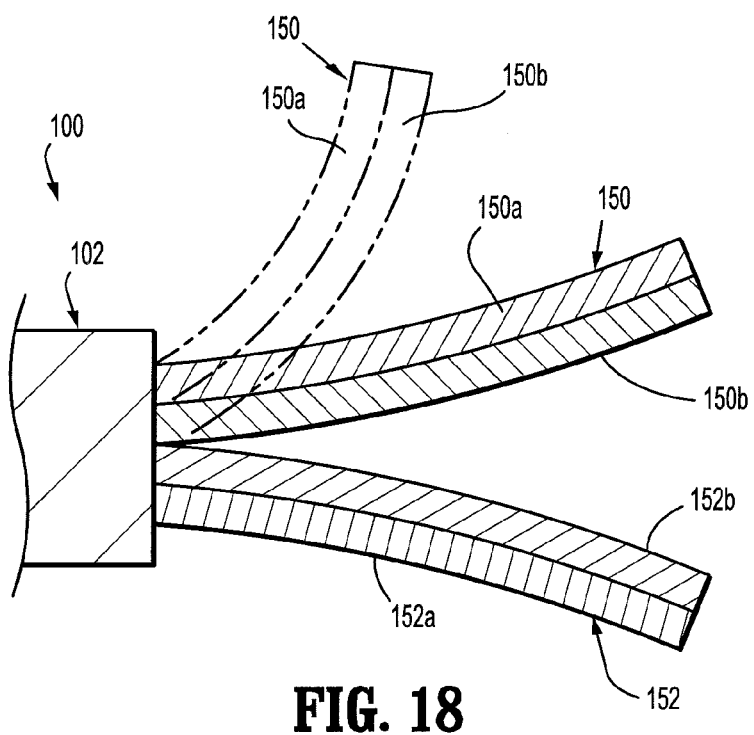
FIG. 18 is an enlarged view of the indicated area of detail of FIG. 17.

Accordingly, with reference to FIG. 18, the difference in material properties between inner layers 150*a*, 152*a* and outer layers 150*b*, 152*b* of membranes 150, 152 cause membranes 150, 152 to curl or bend from the undeployed condition, wherein membranes 150, 152 extend in a substantially radial direction, to a deployed condition, wherein membranes 150, 152 extend in a direction substantially parallel to the central "X" axis (as shown in phantom in FIG. 18).

Figure 20:
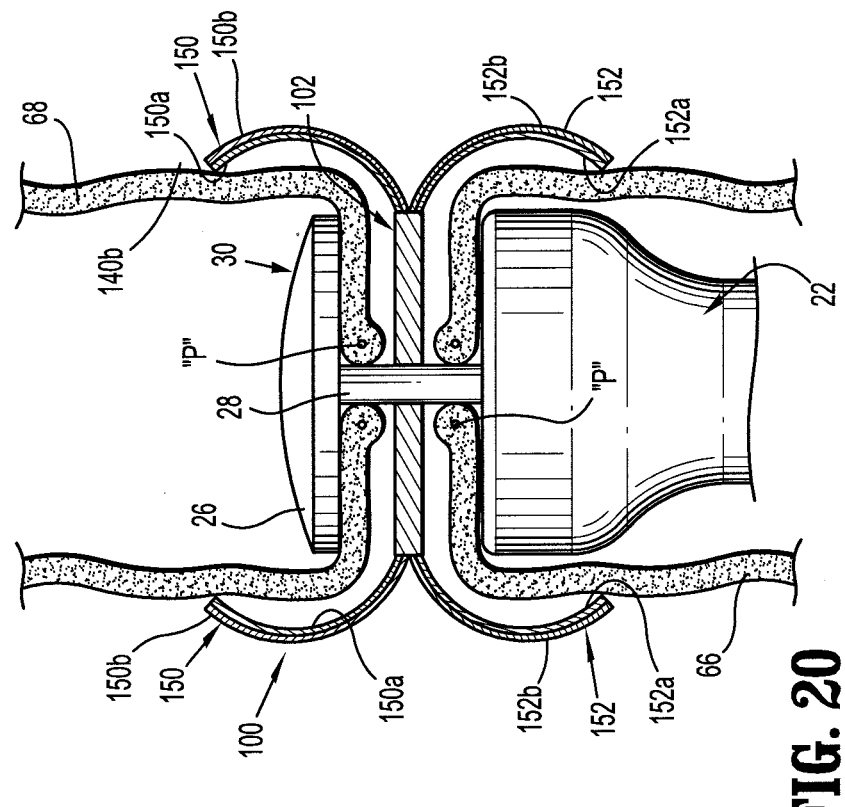
FIG. 20 is a longitudinal cross-sectional view illustrating the anvil rod mounted to the annular stapling device within a surgical site and the support structure of FIGS. 16-18, in a deployed condition, disposed between the apposed surfaces of the tissue.
Figure 19:
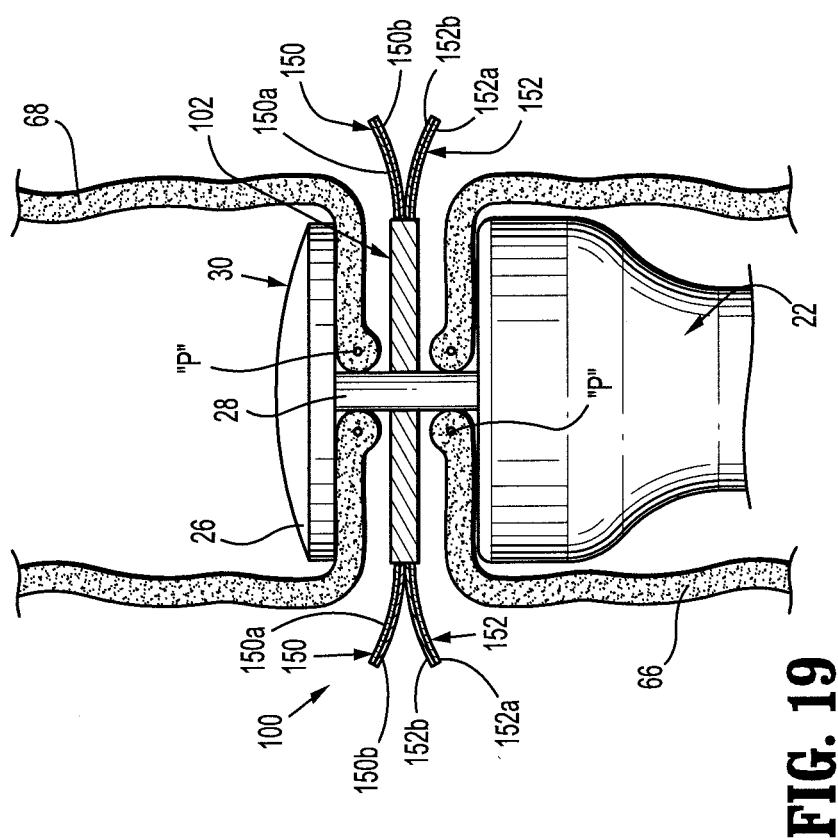
FIG. 19 is a longitudinal cross-sectional view illustrating the anvil rod mounted to the annular stapling device within a surgical site and the support structure of FIGS. 16-18, in an undeployed condition, disposed between the apposed surfaces of the tissue.

Turning now to FIGS. 19 and 20, there is illustrated the use of surgical stapling device 10 and support structure 100 including membranes 150, 152 in an anastomosis procedure to effect joining of intestinal sections 66 and 68. At the point in the procedure shown in FIG. 19, anvil assembly 30 and tubular body portion 20 are shown approximated to one another to capture body portion 102 of annular support structure 100 between intestinal sections 66 and 68, wherein intestinal section 66 and 68 were previously secured about their respective components (e.g., shaft 28 of anvil assembly 30, and the distal end of tubular body portion 20) by conventional means such as a purse string suture "P", annular support structure 100 was positioned between intestinal sections 66 and 68, and anvil assembly 30 was coupled to the distal end of tubular body portion 20.

With body portion 102 of support structure 100 captured between intestinal sections 66, 68, as seen in FIGS. 12 and 13, membranes 150, 152 begin to deploy (i.e., curl or bend from the substantially radially extended orientation to the orientation substantially parallel with the central "X" axis) as described above. In particular, as outer layers 150b, 152b of first and second membranes 150, 152 absorb fluid and swell (i.e., expand), first and second membranes 150, 152 curl or bend to the side of membrane 150, 152 which swells or expands at a rate slower, i.e., toward inner layers 150a, 152a. As membranes 150, 152 are deployed, as indicated by arrow "B", first membrane 150 over-lies intestinal section 68, and second membrane 152 over-lies intestinal section 66, as indicated by arrow "C".

Desirably, membranes 150, 152 extend a predetermined distance over intestinal sections 66 and 68 (e.g., approximately 2 cm). Membranes 150, 152 are arranged so that they will adhere to the surface of intestinal sections 66, 68. Membranes 150, 152 function to inhibit leakage from the anastomosis site and/or function to strengthen or reinforce intestinal sections 66, 68. With membranes 150, 152 deployed, as seen in FIG. 20, surgical stapling device 10 may be fired thereby stapling intestinal sections 66, 68 to one another and cutting the portion of tissue and structure 100 disposed radially inward of the knife, to complete the anastomosis.

Figure 21:
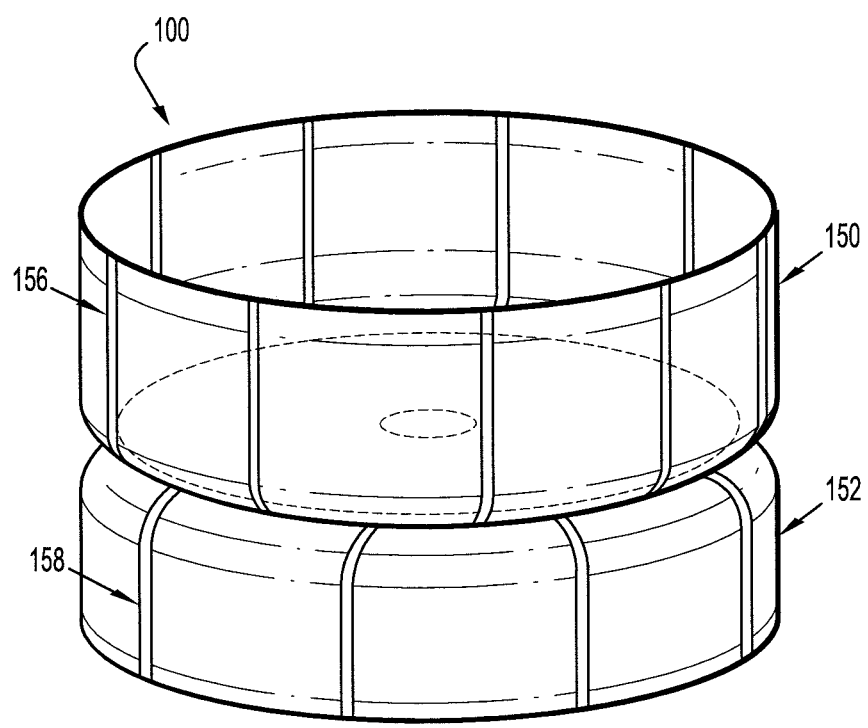
FIG. 21 is a perspective view of a support structure according to yet another alternate embodiment of the present disclosure.

In a further embodiment, as seen in FIG. 21, structure 100 includes a series of ribs 156, 158 provided on and/or in each membrane 150, 152, respectively. Desirably, ribs 156, 158 are spaced radially around the perimeter or circumference of membranes 150, 152. Ribs 156, 158 are substantially axially oriented.

Ribs 156, 158 are fabricated from a shape memory material, alloy or the like, preferably, NITINOL™ and the like. Alternatively, the ribs may be fabricated from a polymeric material. It is further envisioned that ribs 156, 158 may be fabricated from a bio-absorbable or non-absorbable material.

Ribs 156, 158 have a memorized shape which is oriented substantially parallel to the central "X" axis of support structure 100. In this manner, support structure 100 has a first or un-deployed condition in which ribs 156, 158 are in a biased rolled-up or otherwise collapsed condition and membranes 150, 152 are also rolled-up or otherwise collapsed, and a second or deployed condition in which ribs 156, 158 are in their memorized shape or unbiased condition and membranes 150, 152 are extended.

In use, with support structure in an un-deployed condition, support structure 100 is positioned on shaft 28 of anvil assembly 30. With support structure 100 so positioned, support structure 100 is deployed when ribs 156, 158 return to their memorized conditions. In particular, the return of ribs 156, 158 to their memorized conditions extends membranes 150, 152 over intestinal sections 66 and 68 and/or in a direction substantially parallel to the central "X" axis.

Turning now to FIGS. 22-30, a support structure assembly, in accordance with an embodiment of the present disclosure, is generally designated as 180 and is operatively supported on shaft 28 of anvil assembly 30. As mentioned above, anvil assembly 30 includes an anvil member 26 and a shaft 28, extending from anvil member 26 and being operatively connectable with a distal end portion of stapling device 10.

Anvil assembly 30 includes a support structure assembly 180 operatively disposed on shaft 28 thereof. Support structure assembly 180 includes sleeve 160 operatively disposed on shaft 28 of anvil assembly 30. Sleeve 160 includes a proximal portion 1610a having a diameter slightly larger than the diameter of shaft 28, and a distal portion 160b having a diameter larger than the diameter of proximal portion 160a and defining a chamber 162 between shaft 28 and distal portion 160b.

Figure 23:
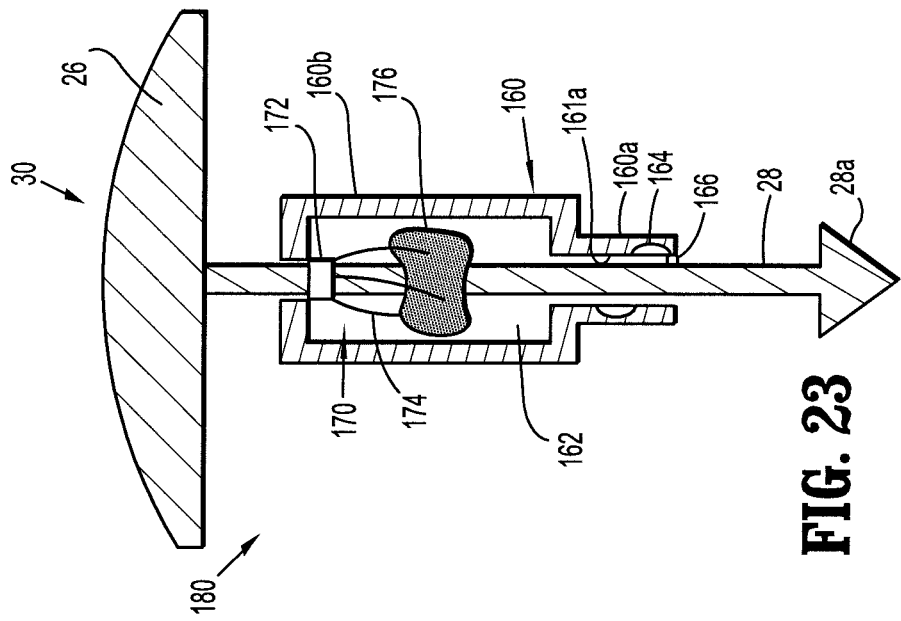
FIG. 23 is a longitudinal cross-sectional view of the support structure assembly of FIG. 22.
Figure 22:
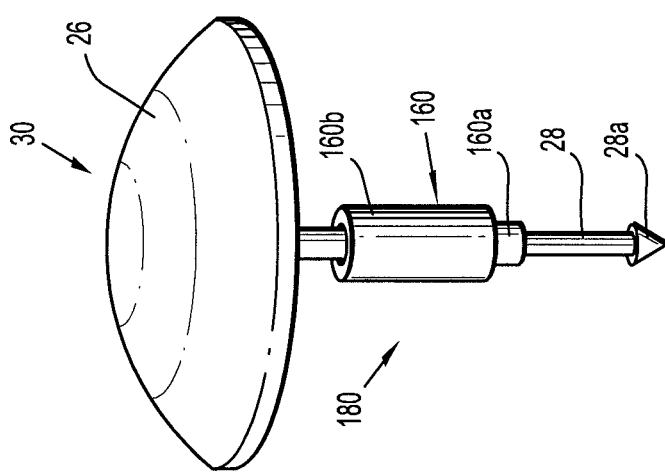
FIG. 22 is a perspective view of an anvil assembly including a support structure assembly, according to another embodiment of the present disclosure, shown in a first condition.
Figure 25:
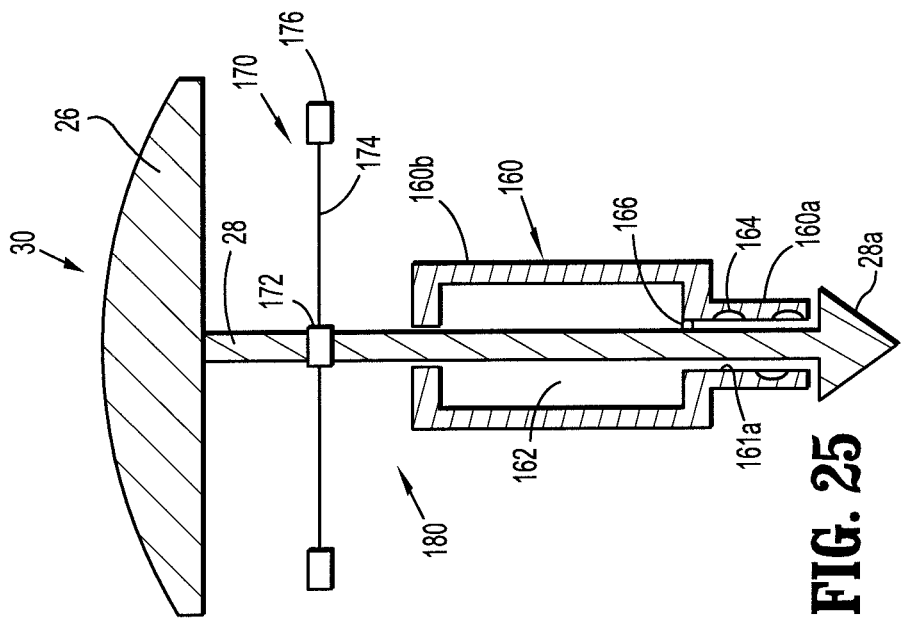
FIG. 25 is a longitudinal cross-sectional view of the support structure of FIG. 24.
Figure 24:
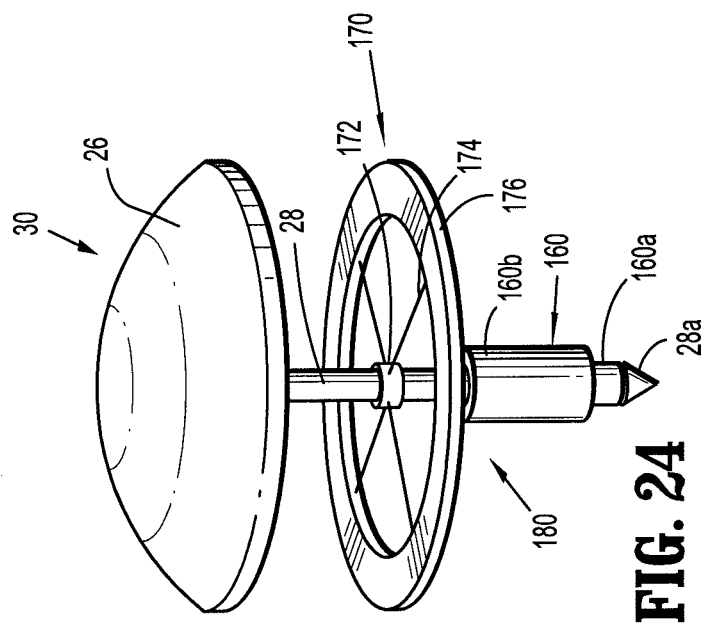
FIG. 24 is a perspective view of the support structure assembly of FIGS. 22 and 23, shown in a second condition.

Sleeve 160 is movable along the length of shaft 28 from a first position in which sleeve 160 is in close proximity to anvil member 30 (see FIGS. 22 and 23) and a second position in which sleeve 160 is spaced a distance from anvil member 28 (see FIGS. 24 and 25). Desirably, a cam surface 164 is formed in an inner surface 161a of proximal portion 160a of sleeve 160. Additionally, a cam follower 166 is provided on shaft 28 and operatively engages cam surface 164 of sleeve 160. Desirably, during use, anvil 26 is drawn closer to the tubular body portion 20, as discussed above. The cam follower 166 rides in cam surface 164 so that sleeve 160 is axially displaced with respect to shaft 28 (e.g., between the first and second positions). Preferably, as shaft 28 is drawn proximally, the cam follower 166 and cam surface 164 interact so that sleeve 160 moves proximally move quickly than shaft 28.

Support structure assembly 180 further includes a support structure 170 operatively supported on shaft 28. Support structure 170 has a collapsed or first condition, as seen in FIG. 23, wherein support structure 170 is retained within chamber 162 of sleeve 160, and an expanded or second condition, as seen in FIGS. 24 and 25, wherein support structure 170 is free from chamber 162 of sleeve 160 and extends radially outward from shaft 28.

As seen in FIGS. 23-28, and in particular FIGS. 26-28, support structure 170 preferably includes a central hub 172, a plurality of spokes 174 extending from hub 172, and a disc 176 operatively connected to the distal end of spokes 174. Desirably, support structure 170 includes a ring 178 operatively connected to the distal end of each spoke 174. Ring 178 and spokes are desirably resilient and collapsible and provides disc 176 with an increased degree of structural integrity. Preferably, spokes 174 and ring 178 are made from a wire of shape memory material (e.g., NITINOL and the like), wherein spokes 174 and/or ring 178 have a memorized shape with the spokes radially oriented with respect to hub 172 and ring 178 having a hoop-like shape.

As best seen in FIGS. 27 and 28, disc 176 preferably includes a first disc 176a disposed on a first side of ring 178, and a second disc 176b disposed on a second side of ring 178. Preferably, discs 176a, 176b have a width sufficient to extend across staple receiving slots 36. In this manner, as will be discussed in greater detail below, when surgical stapling device 10 is fired, staples 38 (see FIGS. 29 and 30) are driven through discs 176a, 176b.

It is contemplated that first and second discs 176a, 176b may be fabricated from any of the materials disclosed above. In an embodiment, first and second discs 176a, 176b are impregnated with a wound treatment material.

Figure 29:
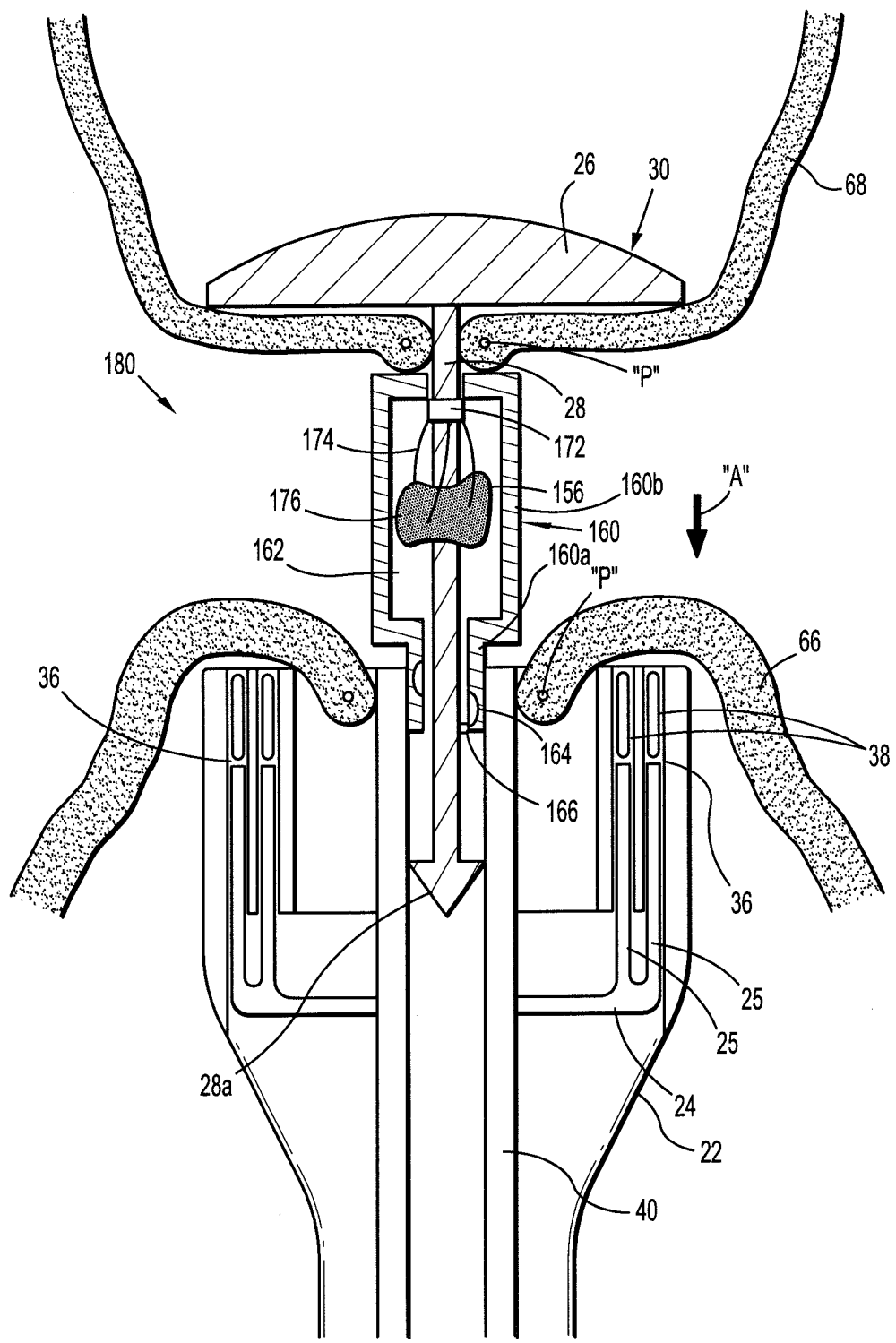
FIG. 29 is a longitudinal cross-sectional view of a distal end of the surgical stapling apparatus while disposed in an operative site, illustrating the support structure of FIGS. 22-28, while in the first condition.
Figure 30:
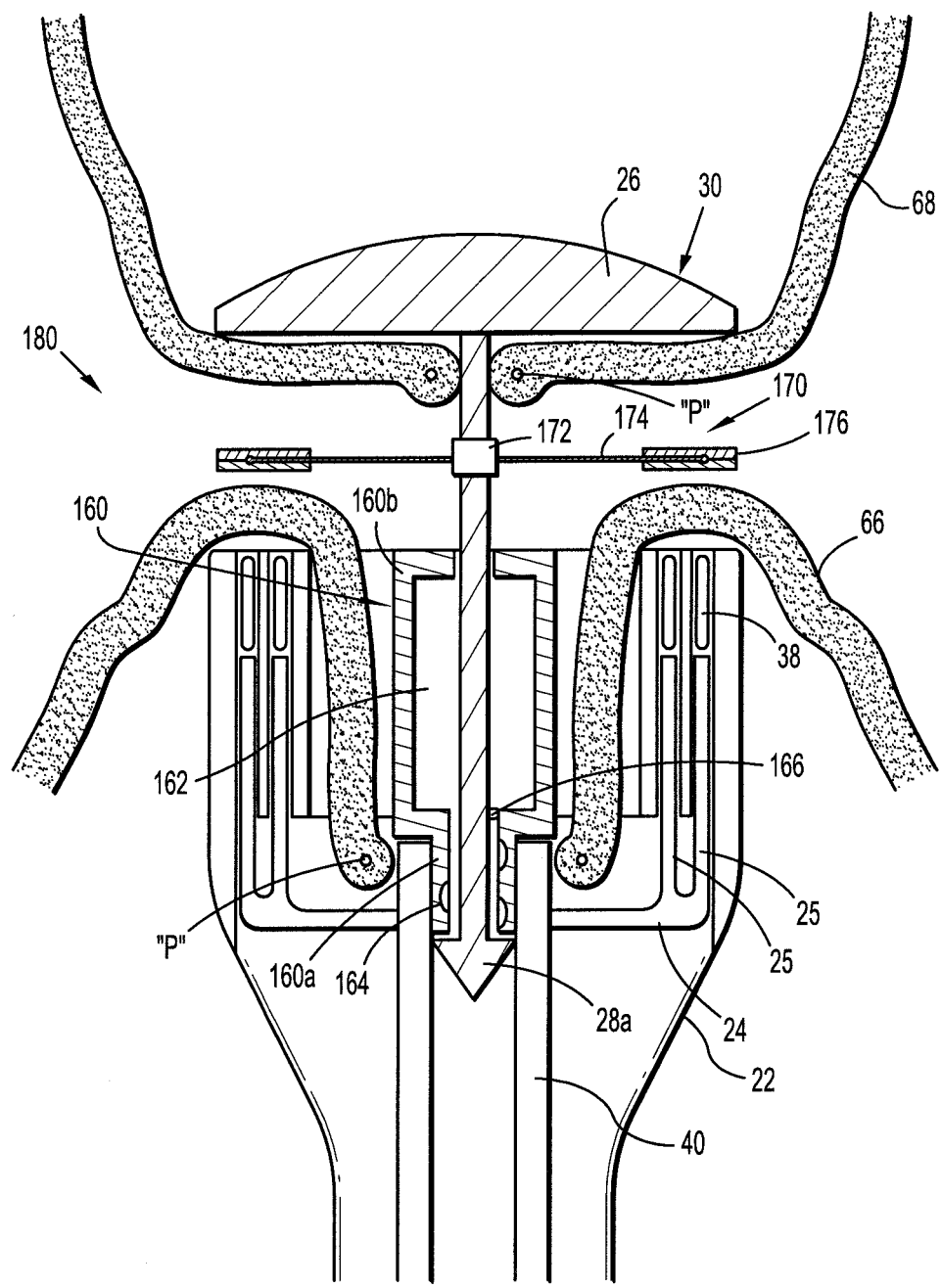
FIG. 30 is a longitudinal cross-sectional view of a distal end of the surgical stapling apparatus while disposed in an operative site, illustrating the support structure of FIGS. 22-28, while in the second condition.
Figure 31:
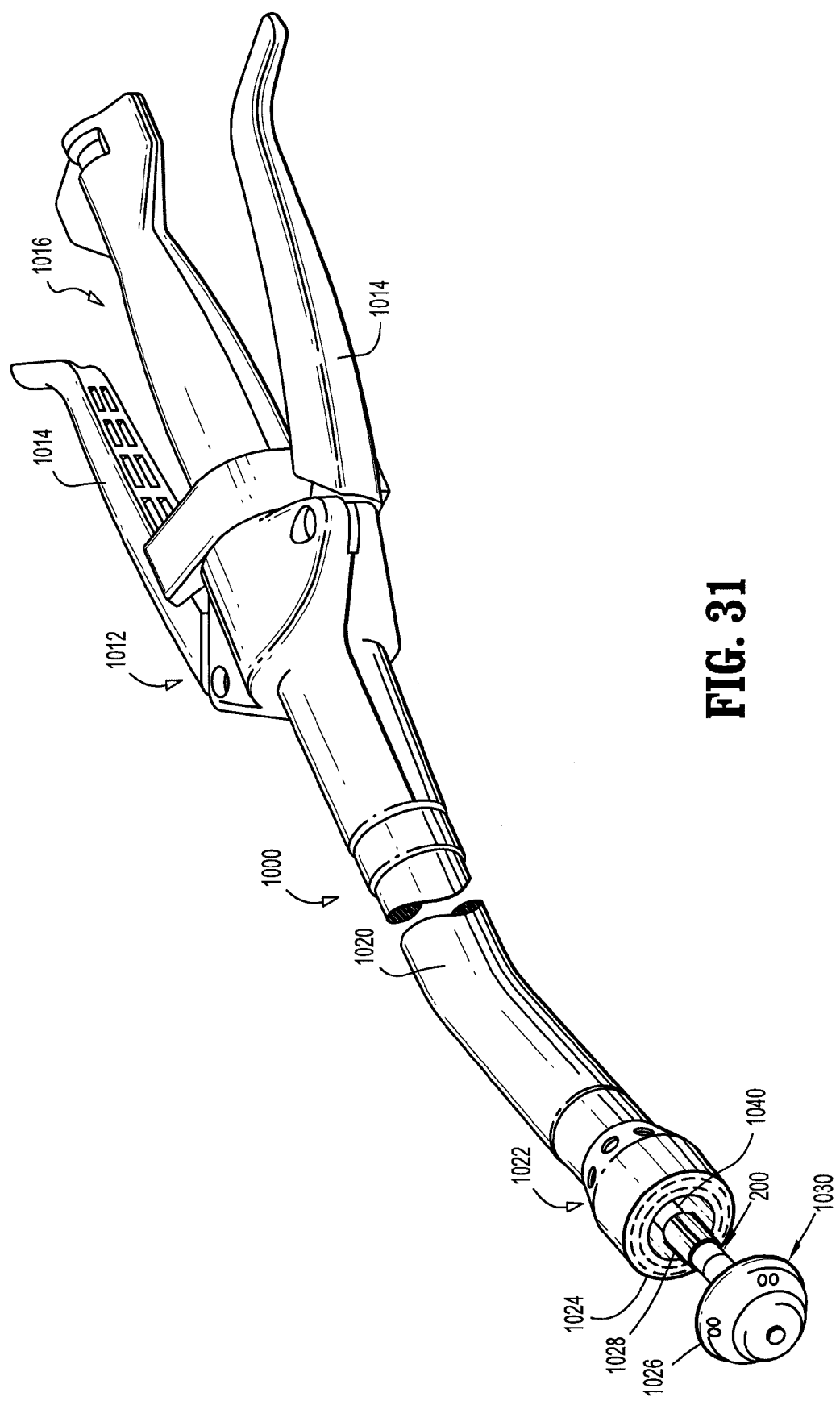
FIG. 31 illustrates a perspective view of a surgical stapling apparatus according to another embodiment of the present disclosure.

Turning now to FIGS. 29 and 30, a method of using support structure assembly 180 is shown and described. The anastomosis procedure is typically performed using minimally invasive surgical techniques including laparoscopic means and instrumentation. At the point in the procedure shown in FIG. 29, a diseased intestinal section has been previously removed, anvil assembly 30 has been applied to the operative site, and distal end 22 of body portion 20 (i.e., the tubular body portion) of surgical stapling apparatus 10 has been inserted into a second intestinal section 68.

According to the present method, following positioning of anvil assembly 30 and the distal end of tubular body portion 20 within intestinal sections 66 and 68, respectively, the surgeon maneuvers anvil assembly 30 until a proximal end of shaft 28 is inserted into a connection member 40 provided in the distal end of tubular body portion 20 of surgical stapling device 10. Connection member 40 desirably connects the proximal end of shaft 28 and proximal portion 160a of sleeve 160 in order to effect the mounting of anvil assembly 30 to tubular body portion 20. Connection member 40 may include a rod 41 disposed within the tubular body portion 20 which has a detent structure for engaging shaft 28.

Thereafter, anvil assembly 30 and tubular body portion 20 are approximated to approximate intestinal sections 66, 68 and move sleeve 160 from the first position to the second position in order to deploy support structure 170. In particular, during approximation of anvil assembly 30 and tubular body portion 20, as seen in FIG. 29, sleeve 160 is moved in a proximal direction, from the first position to the second position (as indicated by arrow "A"), relative to shaft 28, as discussed above.

As sleeve 160 is moved in a proximal direction relative to shaft 28, support structure 170 is exposed from a distal end of sleeve 160. As seen in FIG. 30, once sleeve 160 has moved in the proximal direction relative to shaft 28 by an amount sufficient for the distal end thereof to completely clear support structure 170 or until proximal portion 160a of sleeve 160 abuts against, e.g., bottoms out against, an enlarged head 28a provided at a proximal end of shaft 28, support structure 170 is deployed (i.e., spokes 174 and ring 178 are returned to their memorized or pre-biased conditions).

As seen in FIG. 30, with support structure 170 deployed, disc 176 is expanded between first and second intestinal sections 66, 68 and substantially overlies and/or comes into registration with staple receiving slots 36 of staple cartridge assembly 22. With support structure 170 deployed between first and second intestinal sections 66, 68, anvil assembly 30 is further approximated toward tubular body portion 20 to thereby clamp disc 176 between first and second intestinal sections 66, 68. With anvil assembly 30 fully approximated toward body portion 20, surgical stapling device 10 is fired thereby stapling disc 176 between intestinal sections 66, 68. Additionally, concomitantly therewith, the knife (not shown) is actuated to sever the portion of intestinal sections 66, 68 and the portion of spokes 174 located radially inward from the knife, thereby completing the anastomosis.

From the foregoing, it will be appreciated that disc 176 of support structure 170 functions to strengthen the anastomosis and reduce the occurrence of bleeding, leaking and stricture. It is also to be appreciated that the annular adhesive structures of the present disclosure may be utilized in a number of other applications and is not limited solely to bowel or bronchus anastomosis.

Turning now to FIGS. 31-37, a support structure 200, in accordance with an alternate embodiment of the present disclosure, is shown supported on stem 1028 of anvil member 1026 of annular surgical stapling device 1000. Surgical stapling device 1000 is substantially similar to surgical stapling device 10 and will only be discussed in detail to the extent necessary to identify differences in construction and operation.

Figure 32:
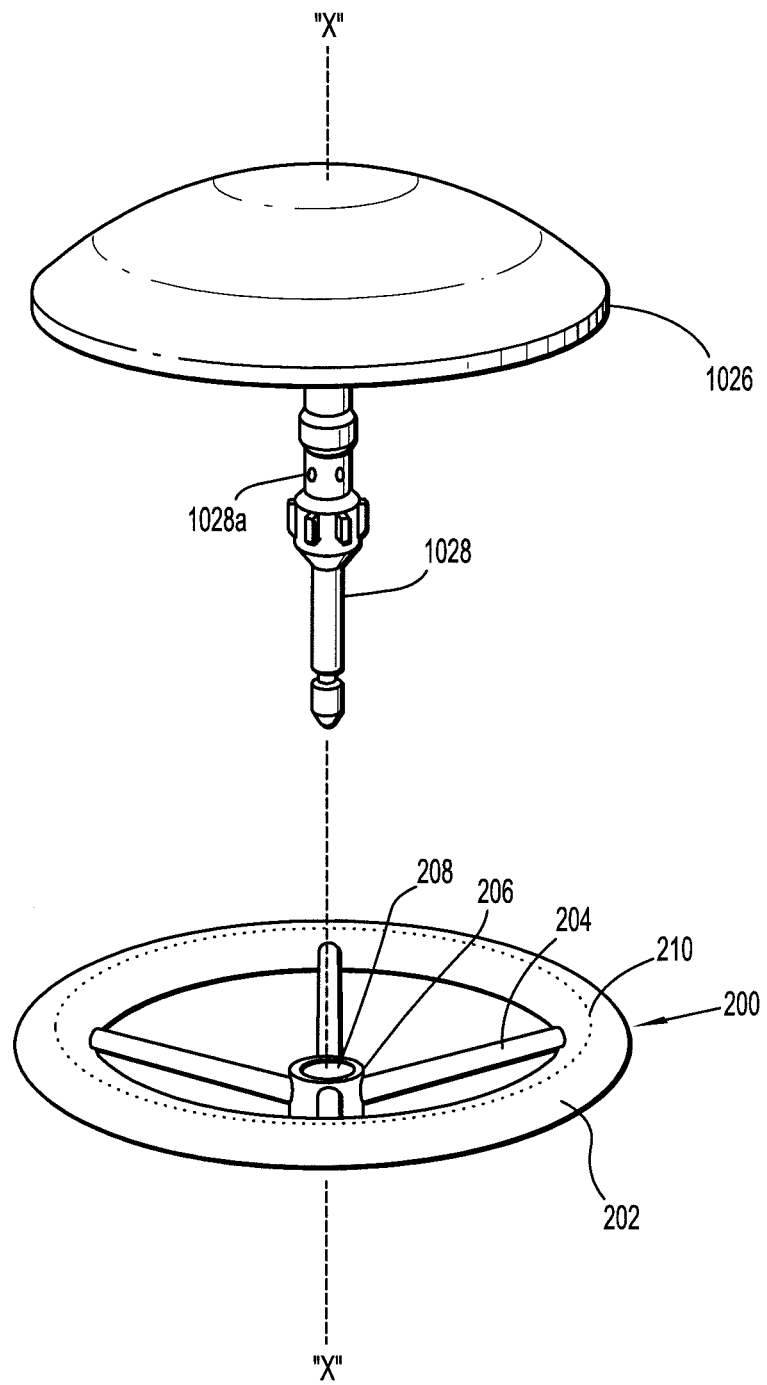
FIG. 32 is a perspective view, with parts separated, of the anvil member of the surgical stapling apparatus of FIG. 31 including a support structure, in accordance with the present disclosure.
Figure 33:
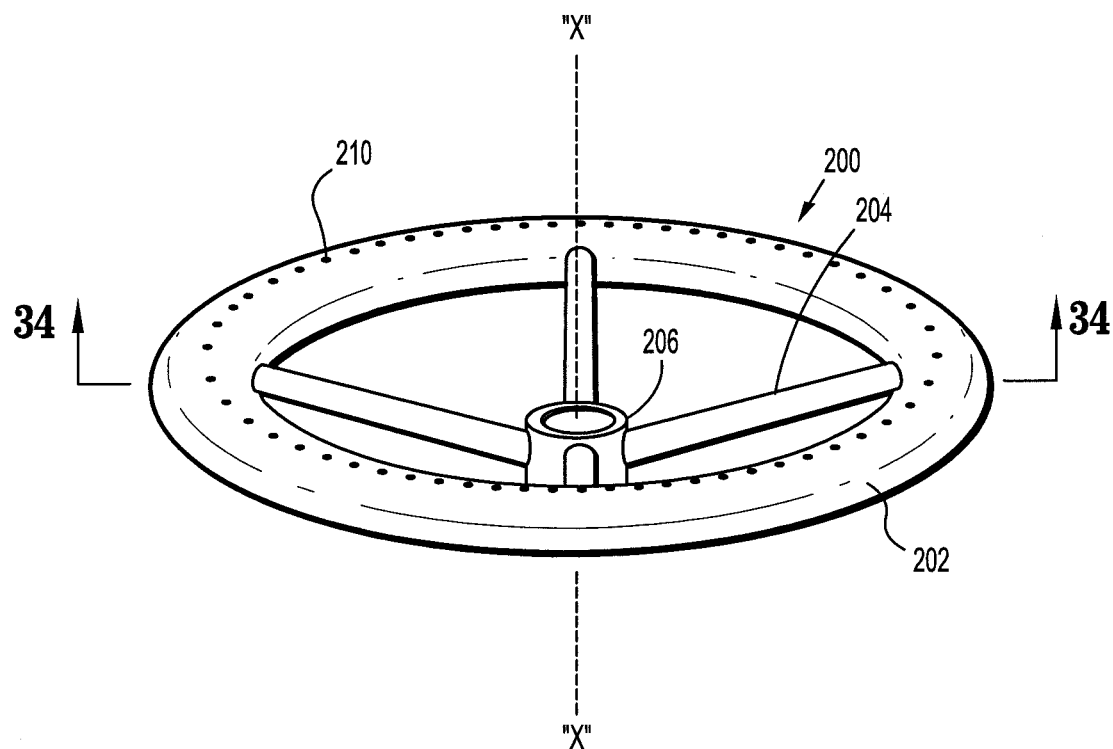
FIG. 33 is a perspective view of the support structure of FIG. 32, illustrated in an expanded condition.
Figure 34:
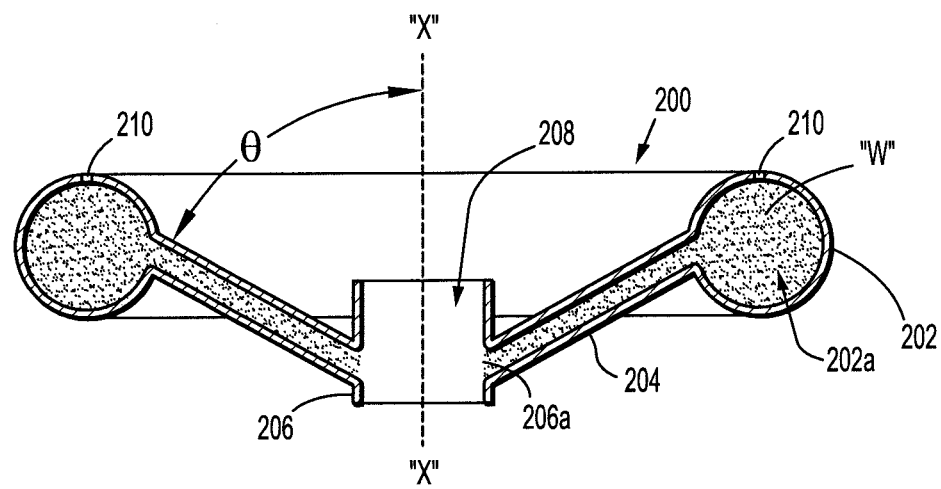
FIG. 34 is a cross-sectional view of the support structure of FIG. 33, as taken through 34-34 of FIG. 33.

As seen in FIGS. 32-34, support structure 200 includes an outer circular rim, tube or doughnut 202, a plurality of spokes 204 extending radially inward from circular tube 202, and a central hub 206 operatively joining spokes 204. Circular tube 202 is generally toroidal in shape when in an expanded condition. Central hub 206 defines a lumen 208 therethrough, having a central longitudinal "X" axis, for receipt of stem 1028 of anvil member 1026.

As seen in FIG. 34, circular tube 202 of support structure 200 defines a cavity 202a therein, and spokes 204 act as conduits for transmitting fluid (e.g., wound treatment material "W") to cavity 202a of circular tube 202. Central hub 206 includes a plurality of apertures 206a formed therein and which are in fluid communication with spokes 204. Apertures 206a of central hub 206 are in fluid communication with ports 1028a (see FIG. 32) formed in stem 1028 of anvil member 1026. Ports 1028a are in fluid communication with a conduit or passage 1028b extending axially through stem 1028 of anvil member 1026. Conduit 1028b is fluidly connected to a source of fluid (not shown), when anvil member 1026 is coupled to connection means 1040 (see FIG. 31), in order to deliver a fluid (e.g., wound treatment material "W") to cavity 202a of circular tube 202.

Support structure 200 has a first unexpanded or deflated condition in which cavity 202a of circular tube 202 is unfilled and circular tube 202 and spokes 204 are wrapped around, collapsed onto, or otherwise in close proximity to stem 1028 of anvil member 1026. Support structure 200 has an expanded condition in which cavity 202a of circular tube 202 is filled with wound treatment material "W".

As seen in FIGS. 32-34, circular tube 202 is provided with a plurality of perforations 210 formed therein. Preferably, perforations 210 are formed along an upper or distal surface 203 of circular tube 202. Additionally, perforations 210 extend at least partially around, and preferably completely around, the circumference or perimeter of circular tube 202. In this manner, as will be described in greater detail below, wound treatment material "W" is dispensed from perforations 210 when circular tube 202 is expanded or inflated with wound treatment material "W".

As seen in FIG. 34, spokes 204 are angled by a degree "Θ" with respect to the longitudinal "X" axis of hub 206. Desirably, spokes 204 are angled in a distal direction when support structure 200 is in an inflated condition. In one embodiment, when support structure 200 is in the inflated condition, spokes 204 are angled by a degree "Θ" and sufficient for circular tube 202 to be in close proximity to a tissue contacting surface of anvil member 1026. Preferably, as will be described in greater detail below, when support structure 200 is in the inflated condition, circular tube 202 will substantially contact the tissue "T" purse string sutured to anvil member 1026.

While support structure 200 has been shown and described as including hub 206, it is envisioned and within the scope of the present disclosure that spokes 204 may be directly connected to stem 1028 and, more particularly, fluidly connected to ports 1028a of stem 1028.

It is envisioned that the wound treatment material "W" can include one or a combination of wound treatment materials, such as adhesives, hemostats, sealants, medicaments and the like as described above.

Figure 37:
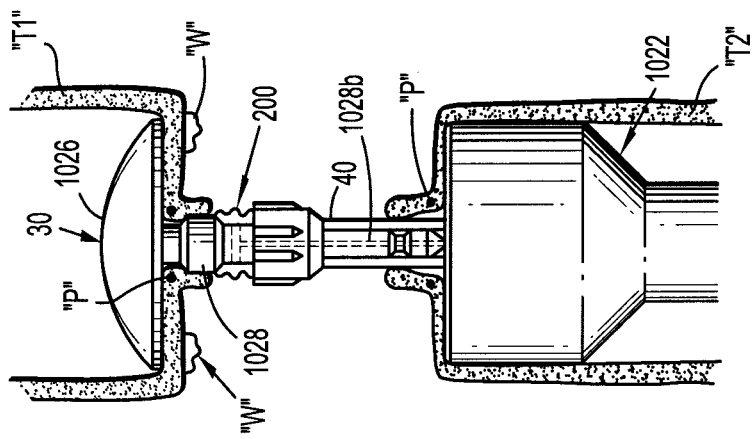
FIG. 37 is a side elevational view of the distal end of the surgical stapling apparatus of FIG. 31, shown positioned in the operative site, illustrating the wound treatment applying structure of FIGS. 32-34 in a third or deflated condition following dispensing of the wound treatment material onto the surface of the tissue to be anastomosed.
Figure 36:
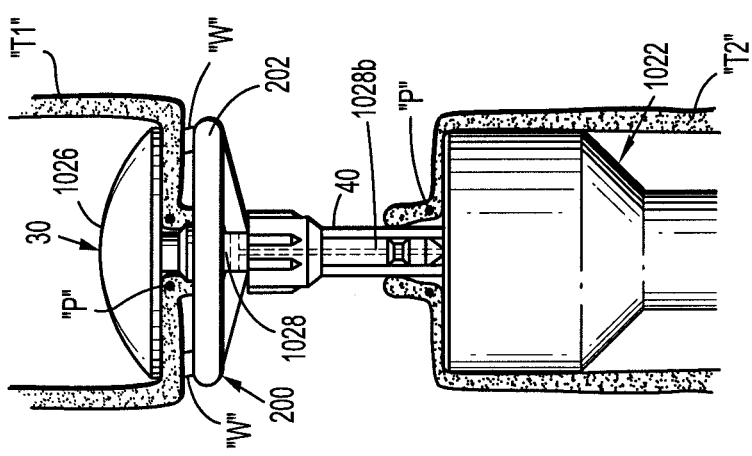
FIG. 36 is a side elevational view of the distal end of the surgical stapling apparatus of FIG. 31, shown positioned in the operative site, illustrating the support structure of FIGS. 32-34 in a second or inflated condition in order to dispense wound treatment material onto the surface of the tissue to be anastomosed.
Figure 35:
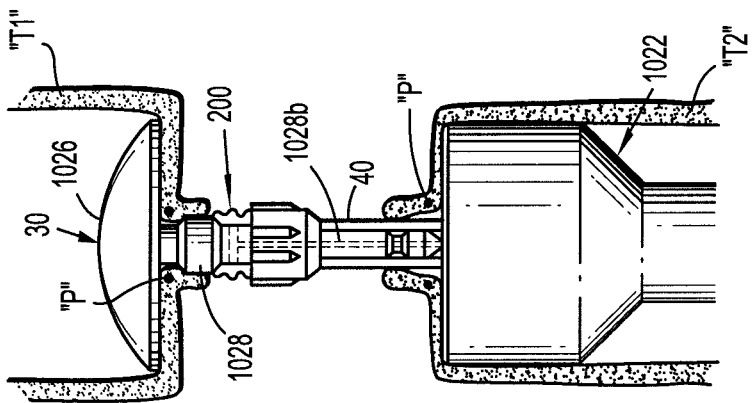
FIG. 35 is a side elevational view of a distal end of the surgical stapling apparatus of FIG. 31, shown positioned in the operative site, illustrating the support structure of FIGS. 32-35 in a first or deflated condition.

Turning now to FIGS. 35-37, a method of using support structure 200 for distributing and/or dispensing wound treatment material is shown and described. The anastomosis procedure is typically performed using minimally invasive surgical techniques including laparoscopic means and instrumentation. At the point in the procedure shown in FIG. 35, a diseased intestinal section has been previously removed, anvil assembly 1030 has been applied to the operative site, and distal end 1022 of body portion 1020 (i.e., the tubular body portion) of surgical stapling apparatus 1000 has been inserted into a second intestinal section "T2".

Following positioning of anvil assembly 1030 and distal end 1022 of body portion 1020 within intestinal sections "T1 and T2", the surgeon maneuvers anvil assembly 1030 until the proximal end of stem 1028 is inserted into the distal end of connection means 1040 to effect mounting of anvil assembly 1030 to connection means 1040. With anvil assembly 1030 mounted to connection means 1040, as seen in FIG. 35, support structure 200 is expanded to the inflated condition by injecting wound treatment material "W", through conduit 1028b of stem 1028, through spokes 204, and into cavity 202a of circular tube 202. The proximal end of the tubular body portion desirably includes a button, plunger or other actuator for dispensing wound treatment material to support structure 200.

As the pressure of wound treatment material "W" within support structure 200 increases, as seen in FIG. 36, circular tube 202 comes into contact with or substantially approaches first intestinal section "T1" and wound treatment material "W" is dispensed from apertures 210. As wound treatment material "W" is dispensed from support structure 200, wound treatment material "W" is deposited on first intestinal section "T1". Preferably, wound treatment material "W" is deposited completely around first intestinal section "T1".

While it is shown and described that support structure 200 is configured to deposit wound treatment material "W" onto first intestinal section "T1", it is envisioned and within the scope of the present disclosure for support structure 200 to be configured to dispense wound treatment material "W" onto second intestinal section "T2".

As seen in FIGS. 36 and 37, following deposition of wound treatment material "W" onto first intestinal section "T1", support structure, and in particular circular tube 202 is deflated by withdrawing wound treatment material "W" through conduit 28b and spokes 204. Support structure 200 may include a suture attached to circular tube 202, which extends through tubular body portion 1022 to the proximal end of apparatus 1000, so that the user in pulling on the suture can collapse and/or remove the structure 200. Alternatively, the support structure 200 may include an elastic, expandable material. With wound treatment material "W" deposited on first intestinal section "T1" and with support structure 200 deflated, anvil member 1026 and tubular body portion 1022 are approximated to approximate first intestinal section "T1" and second intestinal section "T2". The rotatable grip member 1018 is used to approximate the anvil member 1026 and tubular body portion 1022. When first intestinal section "T1" is in contact with second intestinal section "T2", wound treatment material "W" is sandwiched therebetween.

Surgical stapling apparatus 1000 is then fired by operating handle member 1012, thereby stapling first intestinal section "T1" to second intestinal section "T2". Upon firing of surgical stapling apparatus 1000, the staples are expelled from distal end 1022 of body portion 1020 by the staple pusher member (not shown) and driven through first and second intestinal sections "T1 and T2". Additionally, an annular knife, disposed radially inward of the staple pockets 1024, severs the intestinal tissue radially inwardly of the staple pockets 1024, to thereby complete the anastomosis.

In an alternate method, it is envisioned that the surgical anastomosis procedure may be accomplished without staples. Accordingly, following deposition of wound treatment material "W" onto first intestinal section "T1" and/or second intestinal second "T2", anvil member 1026 is approximated toward distal end 1022 of body portion 1020 until first intestinal second "T1" contacts second intestinal section "T2" thereby squeezing wound treatment material "W" therebetween. Depending on the particular wound treatment material "W" (e.g., adhesive) used, anvil member 1026 is maintained approximated against distal end 1022 of body portion 1020 for a time sufficient for wound treatment material "W" to cure and begin to adhere first intestinal section "T1" and second intestinal section "T2" with one another. The choice of wound treatment material "W" (e.g., adhesive) will determine the time required to maintain anvil member 1026 approximated against distal end 1022 of body portion 1020.

From the foregoing, it will be appreciated that support structure 200 functions to strengthen the anastomosis and reduce the occurrence of bleeding, leaking and stricture. It is also to be appreciated that the wound treatment material applying structure of the present disclosure may be utilized in a number of other applications and is not limited solely to bowel or bronchus anastomosis.

In one embodiment, it is envisioned that apertures 210 may be areas where tube 202 has been weakened. In this manner, as the pressure within tube 202 increases during inflation, these weakened areas will open up and become apertures 210 and allow for wound treatment material "W" to be dispensed therefrom.

Figure 38:
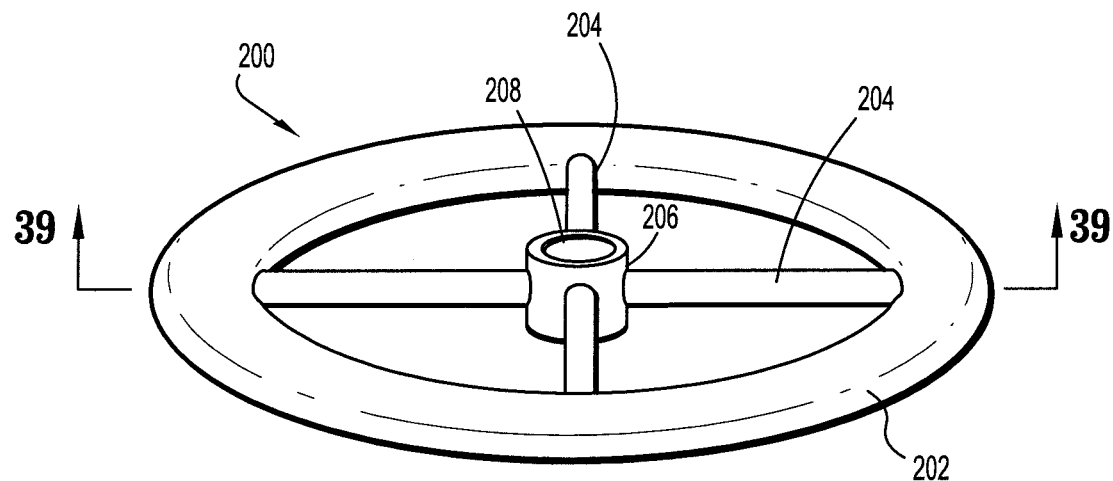
FIG. 38 is a perspective view of a support structure in accordance with another embodiment of the present disclosure, in an expanded condition, for use with the annular surgical stapling device of FIG. 31.
Figure 39:
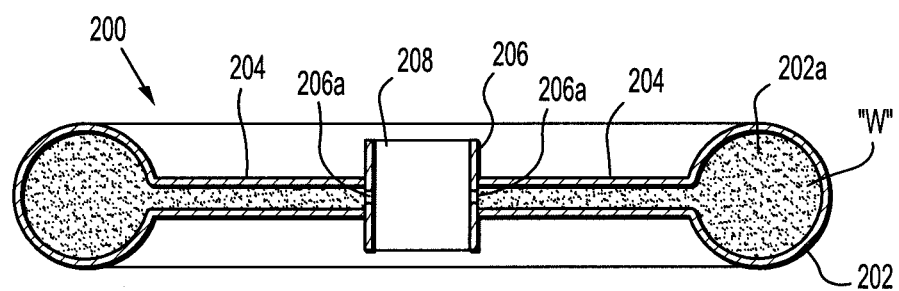
FIG. 39 is a cross-sectional view of the support structure of FIG. 38, as taken through 39-39 of FIG. 38.

As seen in FIGS. 38 and 39, support structure 200 may be fabricated from a polymeric material and may form a circular or "wagon wheel" shaped structure when in the expanded condition. Desirably, spokes 204 extend radially from central hub 206. In the present embodiment, circular tube 202 of support structure 200 does not include apertures 210 formed therein.

In use, structure 200 is inflated at a location between the two layers of tissue to be anastomosed. In this manner, as will be described in greater detail below, when surgical stapling device 1000 is fired, the staples penetrate and/or puncture circular body 202, thereby releasing wound treatment material "W" between the two layers of tissue, and acts to capture circular tube 202 between the two layers of tissue. The firing of surgical stapling device 1000 then drives the knife to sever spokes 204 from the captured circular tube 202, and thereby leave circular tube 202 in position. The circular tube 202, as well as other portions of structure 200, may be formed from bio-absorbable materials. In an alternate method, when the staples puncture circular body 202, the elasticity of support structure 200 causes circular body 202 and spokes 204 to collapse and/or retract back onto hub 206 of shaft 1028 of anvil assembly 1030, in the manner of a popped balloon.

Circular tube 202 may be constructed from any of the materials listed above for the fabrication of structure 100. Circular tube 202 may be reinforced with a mesh or other material in order to thereby provide additional structural integrity and strength. In addition, when the staples penetrate circular tube 202 the staples may capture the mesh and thereby further help to maintain the patency of the lumen between the two layers of anastomosed tissue.

It is contemplated that structure 200 may be used with a two-part adhesive composition by dividing cavity 202a into two separate chambers with each chamber receiving a respective component of the two-part adhesive composition. Alternatively, it is envisioned that a pair of structures 200 may be mounted to shaft 1028 of anvil assembly 1030, with each structure 200 being fluidly connected to a respective component of the two-part adhesive composition.

In the alternative, the structure 200 in FIGS. 38 and 39 may include a collapsible foam that is attached to shaft 1028 and maintained in a collapsed condition. A wound treatment material is delivered to the foam structure through apertures 1028a, thereby expanding the foam. Desirably, the wound treatment material includes a cross-linking material or is reactive with the foam to form an adhesive or sealant material.

Figure 40:
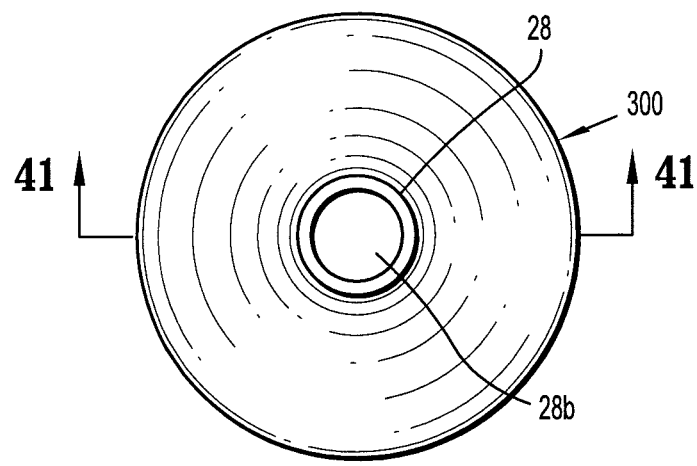
FIG. 40 is a top plan view of a support structure in accordance with another embodiment of the present disclosure, shown in a deployed condition.
Figure 41:
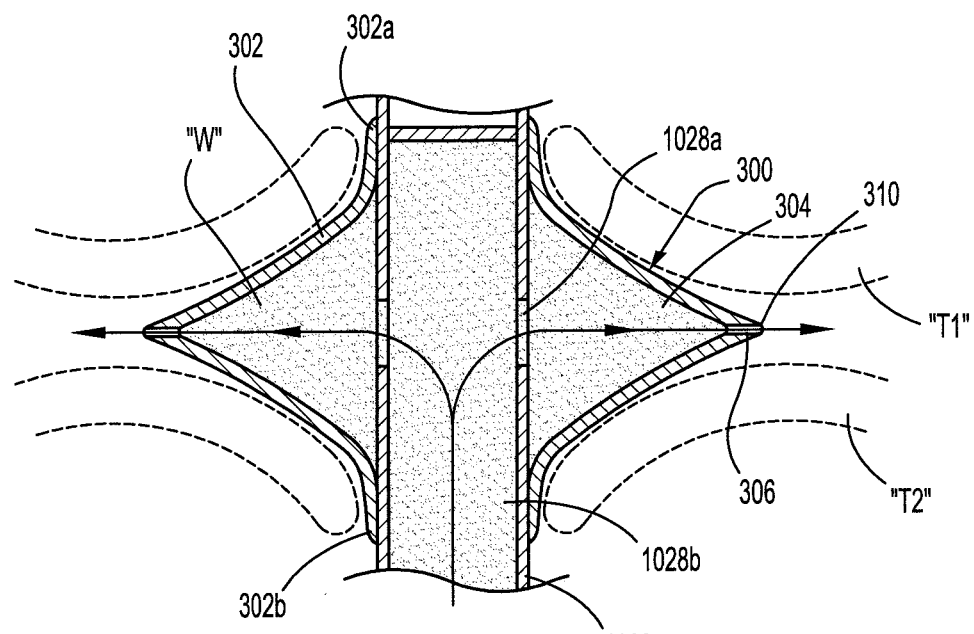
FIG. 41 is a cross-sectional view of the support structure of FIG. 40 as taken through 41-41 of FIG. 40.

Turning now to FIGS. 40 and 41, a support structure, in accordance with an alternate embodiment of the present disclosure, is generally designated as 300. Support structure 300 is generally an annular balloon 302 secured to stem 1028 of anvil member 1026 at a first end 302a and at a second end 302b. Desirably, first end 302a of annular balloon 302 is secured or attached (e.g., adhered) to stem 1028 at a location distal of port 1028a, and second end 302b of annular balloon 302 is secured or attached (e.g., adhered) to stem 1028 at a location proximal of port 1028a. In this manner, as wound treatment material "W" is transmitted through passage 1028b of stem 1028, wound treatment material "W" exits through ports 1028a and fills cavity 304 of annular balloon 302.

As seen in FIG. 41, annular balloon 302 includes a plurality of apertures or perforations 306 formed along a perimetral edge 310 thereof. Accordingly, as wound treatment material "W" fills cavity 304 and the pressure in cavity 304 builds, wound treatment material "W" begins to dispense from perforations 306. Desirably and in accordance with the present disclosure, annular balloon 302 is configured and dimensioned such that perimetral edge 310 and perforations 306 are disposed between adjacent layers of tissue "T1, T2" (shown in phantom in FIG. 41) which are to be secured to one another.

Figure 42:
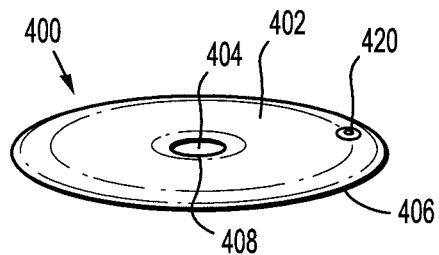
FIG. 42 is a perspective view of a support structure, according to yet another embodiment of the present disclosure, shown in a collapsed or deflated condition.
Figure 43:
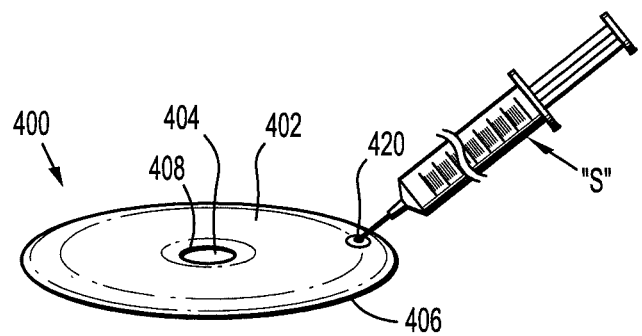
FIG. 43 is a perspective view of the support structure of FIG. 42 being filled or inflated from a remote source of fluid.
Figure 44:
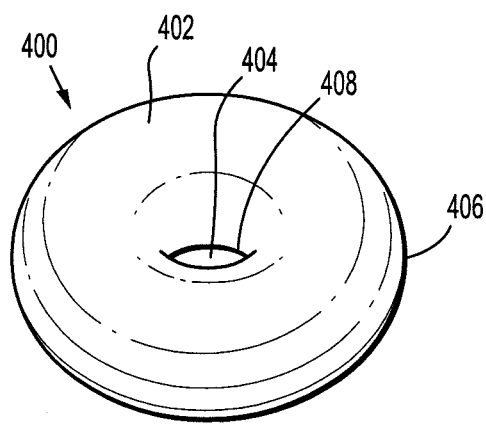
FIG. 44 is a perspective view of the support structure of FIGS. 42 and 43, shown in a filled or inflated condition.

With reference to FIGS. 42-44, a support structure according to yet another embodiment of the present disclosure is generally designated as 400. Structure 400 may be fabricated from any of the materials listed above for the fabrication of structure 100. Structure 400 may have a planar disk-like first, deflated or unexpanded condition, as seen in FIGS. 42 and 43, and a toroidal second, inflated or expanded condition, as seen in FIG. 44.

Structure 400 includes a tubular body portion 402 including a substantially centrally located aperture 404 formed therethrough. Structure 400 is defined by an outer terminal edge 406, and an inner terminal edge 408 defining the size of aperture 404. Structure 400 is sized such that when structure 400 is operatively associated with stapling device 1000, outer terminal edge 406 extends beyond staple retaining pockets 1036 of staple cartridge assembly 1022. Additionally, aperture 404 of structure 400 is sized to at least receive shaft 1028 of anvil assembly 1030 therethrough.

Body portion 402 of structure 400 defines an internal cavity or chamber (not shown) for receiving a wound treatment material, including, and not limited to, a sealant, adhesive, medicament or the like, therein. A port 420 may be provided on body portion 402 through which fluid may be injected into the cavity thereof.

As seen in FIG. 43, a fluid delivery device, in the form of a syringe "S", may be used to inject and/or deliver fluid, in the form of a sealant, adhesive, medicament or the like, to the cavity of body portion 402. As seen in FIG. 44, when structure 400 is inflated with a fluid, structure 400 may have a toroidal shape. While structure 400 is shown in FIG. 44 as having a toroidal shape, when in the inflated condition, it is envisioned and within the scope of the present disclosure the structure 400 may have a washer-like, cylindrical, spherical or other shape, when in the inflated condition.

Similar to structure 200, in use, with adhesive structure 400 in the inflated condition and positioned on shaft 1028 of anvil assembly 1030, tubular body portion 1020 and anvil assembly 1030 are approximated to approximate intestinal sections 66, 68 and capture annular adhesive structure 400 therebetween. Surgical stapling device 1000 is then fired thereby stapling intestinal sections 66, 68 to one another. Upon firing of surgical stapling device 1000, staples are expelled from staple cartridge assembly 1022 and driven through intestinal sections 66, 68 and body portion 402 thereby puncturing body portion 402 and expelling the fluid therefrom.

Figure 45:
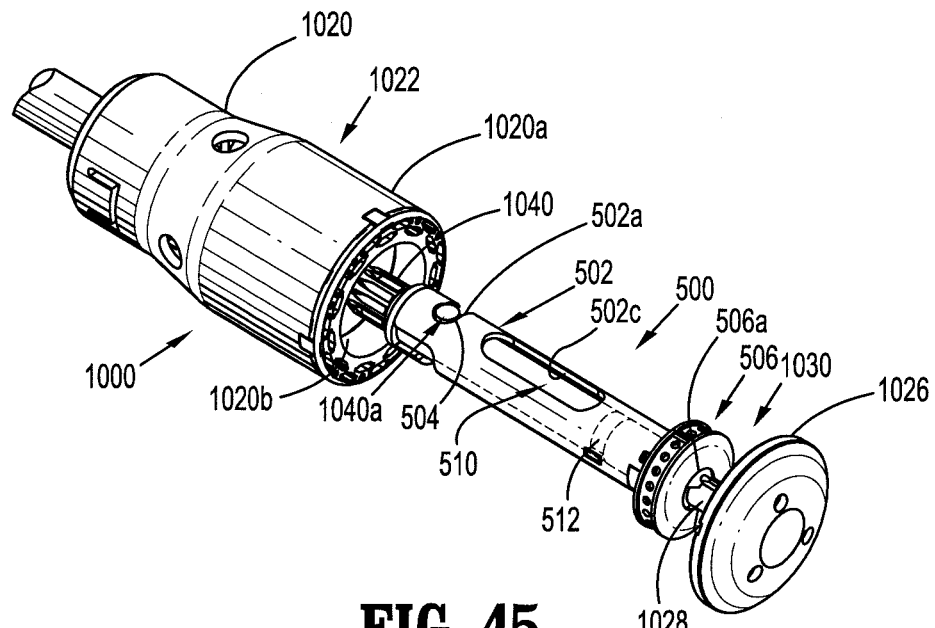
FIG. 45 is an enlarged perspective view of the distal end of the surgical stapling apparatus illustrating an anvil assembly including an applicator operatively connected thereto.
Figure 46:
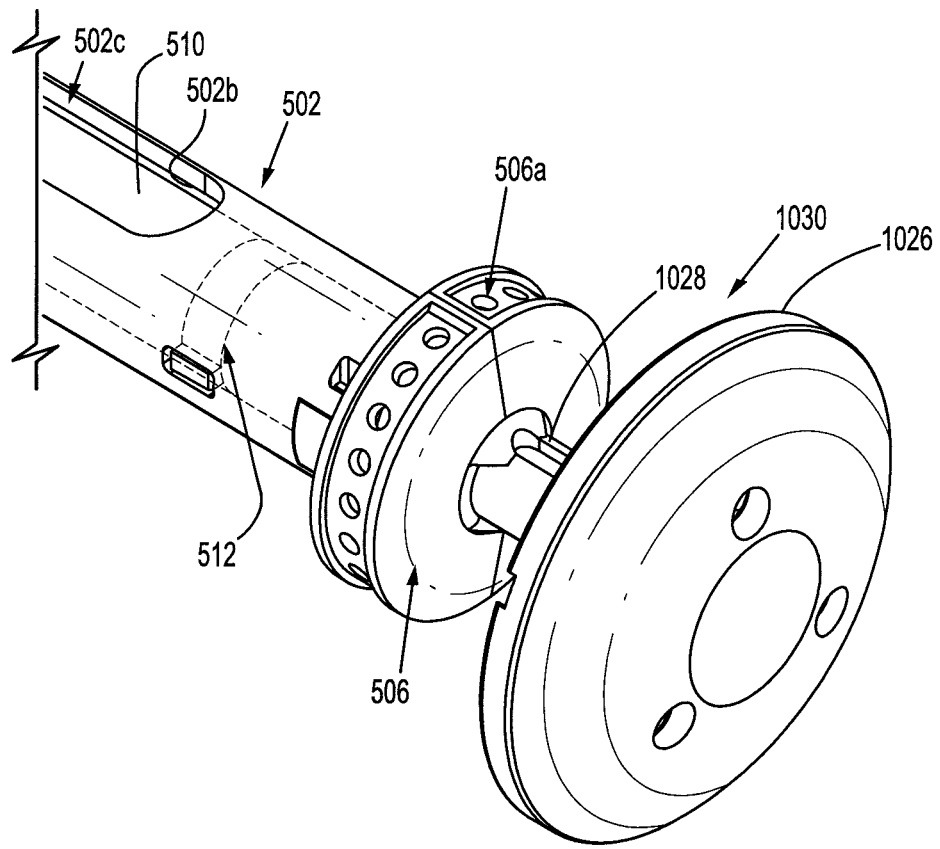
FIG. 46 is an enlarged perspective view of a distal end of the anvil assembly of FIG. 45.

Turning now to FIGS. 45 and 46, an applicator 500, in accordance with an embodiment of the present disclosure, is shown supported on stem 1028 of anvil assembly 1030 of surgical stapling device 1000.

As seen in FIGS. 45 and 46, applicator 500 includes an anvil member 1026 with a tubular sleeve 502 configured and adapted to selectively engage connection member 1040 of surgical stapling device 1000. The connection member 1040 is attached to a shaft 1020a of the tubular body portion 1020. The tubular body portion 1020 also has a recess 1020b formed inwardly of the rows of staples. The remainder of the surgical stapling device 1000 is substantially as discussed above.

A proximal end 502a of sleeve 502 is configured to connect with connection member 1040, using a detent, ¼ turn lock, threaded connection, latch, or bayonet-type connection. For example, connection member 1040 of surgical stapling instrument 1000 is inserted into the proximal end of sleeve 502 and rotated in order to lock applicator 500 and anvil assembly 1030 onto connection member 1040 of surgical stapling device 1000. In particular, sleeve 502 may include an L-shaped slot 504 configured and dimensioned to slidably receive a nub 1040a of connection member 1040.

Applicator 500 includes a manifold 506 disposed between the anvil member 1026 and body portion 1020. The manifold 506 is supported on a distal end of sleeve 502. Manifold 506 may be in the form of a disc having a center which is substantially aligned with a longitudinal axis of stem 1028 of anvil assembly 1030. It is contemplated that manifold 506 has an outer diameter which is less than the outer diameter of anvil 1026.

Manifold 506 includes a plurality of radially oriented channels 506a formed therein. Each channel 506a is in fluid communication with the interior of sleeve 502. Channels 506a of manifold 506 may be in fluid communication with ports 1028a (see FIG. 32) formed in stem 1028 of anvil assembly 1030, which ports 1028a may be in fluid communication with sleeve 502. The manifold, which is desirably formed from a substantially rigid material, is dimensioned to terminate inwardly of the rows of staples. In FIG. 45, the channels 506a are open at the lateral sides of the manifold 506. In other embodiments, the channels 506a may be open on the distal-most or proximal-most surface of the manifold.

The interior of the tubular sleeve 502 forms a chamber 502b for an ampoule of the applicator 500. Ampoule 510 is configured and adapted to retain a quantity of wound treatment material therein. For example, it is envisioned that the wound treatment material can include one or a combination of wound treatment materials, such as adhesives, hemostats, sealants, medicaments and the like as described above. The tubular sleeve 502 may include an aperture or window 502c through which the ampoule 510 may be viewed. The state of the ampoule 510 as full or partially or completely dispensed may be viewed through aperture or window 502c. The ampoule 510 desirably comprises a plastic cartridge that is arranged to direct the wound treatment material in a distal direction, toward the manifold 506, and away from the aperture or window 502c.

In is envisioned and contemplated that ampoule 510 is actuatable to dispense the wound treatment material contained therein into sleeve 502. In particular, upon actuation of ampoule 510, the wound treatment material contained therein is dispensed into sleeve 502 and further on into channels 506a of manifold 506. In this manner, wound treatment material may be dispensed into the target surgical site.

Applicator 500 may further include a seal 512 interposed between ampoule 510 and sleeve 502 in order to ensure that the wound treatment material is efficiently directed into channels 506a of manifold 506.

It is envisioned and contemplated that a driver (not shown) may advance a plunger (not shown) through ampoule 510 in order to force the wound treatment material out of ampoule 510 and through channels 506a of manifold 506. Alternatively, an interior threaded shaft may be used to approximate sleeve 502 with respect to shaft 1020a, thereby compressing ampoule 510 to force wound treatment material out of ampoule 510.

Reference may be made to U.S. application Ser. No. 11/250,277, filed Oct. 14, 2005, the entire contents of which is hereby incorporated herein by reference, for a more detailed description of the ampoule configured for retention of a wound treatment material therein.

A method of using surgical stapling device 1000, including applicator 500 is now described. Following positioning of anvil assembly 1030 and distal end 1022 of body portion 1020 within intestinal sections "T1" and "T2", and securing the anvil assembly 1030 and distal end 1022 to the intestinal sections "T1" and "T2", the surgeon maneuvers anvil assembly 1030 until the proximal end of sleeve 502 is slid over connection member 1040 and locks anvil assembly 1030 onto connection member 1040 of surgical stapling device 1000.

With anvil assembly 1030 mounted to connection means 1040, anvil member 1026 and tubular body portion 1022 are approximated to approximate first intestinal section "T1" and second intestinal section "T2". The rotatable grip member 1018 is used to approximate the anvil member 1026 and tubular body portion 1022. It is contemplated that first intestinal section "T1" and second intestinal section "T2" are approximated such that a radially outer edge of manifold 506 is located in close proximity to at least one of first intestinal section "T1," second intestinal section "T2", and/or the interface therebetween.

When first intestinal section "T1" is in close proximity to second intestinal section "T2", applicator 500 may be actuated to dispense the wound treatment material onto first intestinal section "T1" and/or second intestinal section "T2". For example, a button, plunger or other actuator may be provided on the handle assembly of the device 100 for forcing the wound treatment material out of ampoule 510, into sleeve 502, through ports 1028a, and out through channels 506a of manifold 506.

As wound treatment material "W" is dispensed from applicator 500, wound treatment material "W" is deposited on first intestinal section "T1". Preferably, wound treatment material "W" is deposited completely around first intestinal section "T1" and/or second intestinal section "T2". In certain embodiments, the wound treatment material is dispensed outwardly from the manifold 506. In other embodiments, the wound treatment material is dispensed in a distal and/or proximal direction from the manifold 506, depending on the location of the channels 506a.

Following dispensing of the wound treatment material onto first intestinal section "T1" and/or second intestinal section "T2", anvil member 1026 and tubular body portion 1022 are further approximated to approximate first intestinal section "T1" and second intestinal section "T2" into contact with one another. The manifold is accommodated in the recess 1020b. The rotatable grip member 1018 is once again used to approximate the anvil member 1026 and tubular body portion 1022. When first intestinal section "T1" is in contact with second intestinal section "T2", the wound treatment material is sandwiched therebetween.

Surgical stapling apparatus 1000 may then be fired by operating handle member 1012, thereby stapling first intestinal section "T1" to second intestinal section "T2". Upon firing of surgical stapling apparatus 1000, the staples are expelled from distal end 1022 of body portion 1020 by the staple pusher member (not shown) and driven through first and second intestinal sections "T1 and T2". Additionally, an annular knife, disposed radially inward of the staple pockets 1024, severs the intestinal tissue radially inwardly of the staple pockets 1024, to thereby complete the anastomosis. In other embodiments, the wound treatment material is dispensed after the approximation and/or firing of staples.

In an alternate method, it is envisioned that the surgical anastomosis procedure may be accomplished without staples. Accordingly, following dispensing of the wound treatment material onto first intestinal section "T1" and/or second intestinal second "T2", anvil member 1026 is approximated toward distal end 1022 of body portion 1020 until first intestinal second "T1" contacts second intestinal section "T2" thereby squeezing the wound treatment material therebetween. Depending on the particular wound treatment material (e.g., adhesive) used, anvil member 1026 is maintained approximated against distal end 1022 of body portion 1020 for a time sufficient for the wound treatment material to cure and begin to adhere first intestinal section "T1" and second intestinal section "T2" with one another. The choice of the wound treatment material (e.g., adhesive) will determine the time required to maintain anvil member 1026 approximated against distal end 1022 of body portion 1020.

From the foregoing, it will be appreciated that the structures of the present disclosure function to strengthen the anastomosis and reduce the occurrence of bleeding, leaking and stricture. It is also to be appreciated that the structures of the present disclosure may be utilized in a number of other applications and is not limited solely to bowel or bronchus anastomosis.

In further embodiments, the structures disclosed above are utilized to adhere the intestinal sections to one another without the use of staples. The adhesive material carried by or incorporated in the body portion of the structure joins the intestinal sections and may also provide a seal against leakage. The device 10 is utilized to approximate the intestinal sections and dispose the structure between the intestinal sections, except that the device 1000 need not house staples therein.

Each structure described above is constructed to deliver a predetermined amount of wound treatment material to the target surgical site. The amount of material to be delivered is site specific. Accordingly, different sized (e.g., different thickness or different volume) structures are contemplated for retaining a different volume or quantity of adhesive therein. In this manner, depending on the particular need and the particular surgical procedure, the surgeon may select a structure containing the needed and/or desired volume or quantity of adhesive therein.

While several particular forms of the structures have been illustrated and described, it will also be apparent that various modifications can be made without departing from the spirit and scope of the present disclosure. For example, it is envisioned and within the scope of the present disclosure for an energy-activated wound treatment material, such as, an ultraviolet light activated adhesive, to be used in connection with any of the structures described above. In use, either prior to or following firing of surgical stapling device 10, energy is applied to the structure. For example, a structure including a UV light-curable adhesive is irradiated with UV light to thereby activate the adhesive.

According to one aspect of the present disclosure, an assembly for disposing a support structure between intestinal sections is provided. The assembly includes an annular surgical stapling device, having an anvil assembly and a tubular body portion. The anvil assembly has an anvil member and a first shaft. The tubular body portion carries a plurality of surgical staples in an annular configuration. The tubular body portion has a second shaft disposed radially inward of the surgical staples. The first shaft of the anvil member is attachable to the second shaft of the tubular body. The assembly further includes a support structure having a generally centrally located aperture for being disposed on one of the first shaft and the second shaft. The support structure includes a material selected from the group consisting of at least one of an adhesive, a sealant, a hemostat, and a medicament.

The support structure is impregnated with the material. The support structure includes an inflatable annular structure and is deployable from a first collapsed position to a second expanded position. Wherein, when in the expanded position, the support structure has a toroidal shape defining an interior space for receiving the material. The annular structure may include a circular tube and a plurality of spokes extending radially inwardly from the circular tube. The interior space of the support structure contains the material.

The material may include a first part of a two-part adhesive and is disposed in a first chamber of the interior space of the support structure. A second part of the two-part adhesive is disposed in a second chamber of the interior space of the support structure. The first part and second part of the material is released from the support structure upon deployment of the staples. The staples may have a second part of the two-part adhesive.

The support structure includes a shape memory material and is deployable from a first collapsed position to a second expanded position. The support structure includes a shape memory alloy.

The support structure may include a first layer and a second layer. The first layer includes a first part of a two-part adhesive and the second layer includes a second part of the two-part adhesive.

The support structure may include a first part of a two-part adhesive and a second part of the two-part adhesive may include a liquid to be applied to the support structure.

According to another aspect of the present disclosure, a method of disposing a structure between tissue sections is provided. The method includes the steps of providing a surgical stapling device having an anvil assembly and a body portion. The anvil assembly has an anvil member and the body portion carrying a plurality of surgical staples and a knife. The method further includes the steps of inserting the anvil assembly into a first tissue section; inserting the body portion in a second tissue section; and disposing a support structure between the first tissue section and the second tissue section, the annular structure including a wound treatment material. The method further including the steps of approximating the anvil assembly and body portion with one another so that an end portion of the first tissue section, an end portion of the second tissue section and the support structure are disposed between the anvil member and the body portion, the support structure being disposed between the first tissue section and the second tissue section; deploying the staples from the body portion; and cutting the first tissue section and the second tissue section with the knife.

The anvil assembly may have a first shaft and the body portion may have a second shaft, wherein the first shaft is attachable to the second shaft. The method further including the step of attaching the first shaft to the second shaft before the step of approximating.

The support structure may have an annular shape and include a generally centrally located aperture. The method further includes the step of inserting one of the first shaft and the second shaft into the aperture before the step of attaching the first shaft to the second shaft. The support structure may be disposed on one of the first shaft and the second shaft before the step of approximating.

The support structure includes a shape memory material and is deployable from a first collapsed position to a second expanded position. The support structure is deployed from the first position to the second position before the step of approximating.

The support structure includes an interior space housing a wound treatment material. The wound treatment material is deployed from the interior space upon deployment of the staples.

The wound treatment material is selected from the group consisting of an adhesive, a sealant and a medicament.

The method further includes the step of deploying an adhesive material. The support structure may include a first layer and a second layer. The step of deploying an adhesive material may include contacting the first layer and the second layer. The support structure may include a first part of a two-part adhesive. Accordingly, the step of deploying an adhesive material may include deploying a second part of the two-part adhesive before the step of approximating. The step of deploying an adhesive material includes puncturing the support structure, wherein the support structure having an interior space containing an adhesive therein.

According to a further aspect of the present disclosure, an assembly for joining tissue is provided. The assembly includes an anvil and a body portion juxtaposed with respect to one another along a shaft and arranged so as to be approximated with respect to one another; and a support structure including a resilient material.

The support structure may include a mesh-like material and the resilient material is woven into the mesh of the support structure. The support structure includes a first layer and a second layer. The resilient material may be disposed between the first layer and the second layer.

The first layer of the support structure includes a first part of a two-part wound treatment material, and the second layer of the support structure includes a second part of the two-part wound treatment material.

The support structure includes a first part of a two-part wound treatment material and a second part of the two-part wound treatment material may include a liquid to be applied to the support structure.

According to one aspect of the present disclosure, an assembly for joining tissue is provided. The assembly includes an anvil and a body portion juxtaposed with respect to one another along a shaft and arranged so as to be approximated with respect to one another; and a support structure on the shaft, the support structure defining a cavity for containing a wound treatment material therein. The support structure may be bio-absorbable.

The body portion may carry a plurality of surgical staples in a circular configuration. The surgical staples are deployable against the anvil. The assembly further includes an annular knife disposed radially inwardly of the staples.

The support structure includes an inflatable circular tube. The support structure is deployable from a first collapsed condition to a second expanded condition. The shaft includes at least on port in communication with the cavity for delivering wound treatment material. The wound treatment material expands the support structure from a first collapsed condition to a second expanded condition. The interior space of the circular tube defines a first chamber for receiving a first part of a two-part wound treatment material. The interior space of the circular tube defines a second chamber for receiving a second part of the two-part wound treatment material.

The plurality of surgical staples may have a second part of the two-part wound treatment material.

A support structure for use with an annular stapling apparatus in performing an anastomosis is provided. The support structure includes a disk shaped body portion having an upper surface, a lower surface, an outer terminal edge, and an inner terminal edge defining an aperture therein, the body portion defining a central axis through the aperture; and a first and a second membrane extending radially outward from the outer terminal edge of the body portion.

The inner terminal edge of the body portion extends radially inward of an inner radial edge of a staple cartridge assembly of the stapling apparatus when the support structure is positioned on a shaft of an anvil assembly of the stapling apparatus. The aperture of the body portion is dimensioned to receive a shaft of an anvil assembly.

Each of the first and second membranes is made from a polymeric film. Desirably, each of the first and second membranes is made from polyethylene.

The support structure may have an undeployed condition wherein the first and second membranes are rolled-up towards the body portion, and a deployed condition wherein the first membrane extends in a substantially distal direction from the body portion and the second membrane extends in a substantially proximal direction from the body portion.

The support structure further includes a rip-cord rolled-up into each of the first and second membranes when the support structure is in the undeployed condition. Each rip-cord includes a free end extending from the rolled-up membranes when the support structure is in the undeployed condition. Accordingly, pulling on a rip-cord causes a respective one of the first and second membranes to un-roll. Each of the first and second membranes extends approximately 2.0 cm when un-rolled.

Each membrane includes a first inner layer and a second outer layer. The second outer layer of each membrane swells at a rate greater than the first inner layer.

The support structure may have an undeployed condition wherein the first and the second membranes extend substantially radially outward from the body portion, and a deployed condition wherein the first membrane extends in a substantially distal direction from the body portion and the second membrane extends in a substantially proximal direction from the body portion. Accordingly, when the support structure is in the undeployed condition, the second outer layers of the first and second membranes are in juxtaposed relation to one another.

The second outer layers of the first and second membranes are made from a hydrogel. The first inner layer of each of the first and second membranes is constructed from a substantially non-absorbable material. The first inner layer of each of the first and second membranes is fabricated from a bio-absorbable mesh fabric. Accordingly, when the support structure is positioned on a shaft of an anvil assembly and the anvil assembly is approximated toward a staple cartridge assembly, the support structure is disposed between adjacent tissue sections to be anastomosed. Additionally, when the support structure is disposed between the adjacent tissue sections, as second inner layers of first and second membranes absorb moisture, the first and second membranes curl in the direction of the first inner layer of respective first and second membranes such that the first outer layer contacts a respective tissue section.

According to yet another aspect of the present disclosure, a method of disposing a support structure between adjacent intestinal sections is provided. The method includes the steps of providing an annular surgical anastomosis device. The annular surgical anastomosis device includes an anvil assembly having an anvil member and a first shaft; and a tubular body portion having an annular knife operatively disposed therein and a second shaft disposed radially inward of the annular knife. The first shaft of the anvil assembly is selectively attachable to the second shaft of the tubular body.

The method further includes the steps of inserting the anvil assembly into a first intestinal section; inserting the tubular body portion into a second intestinal section; disposing a support structure between the first intestinal section and the second intestinal section; approximating the anvil assembly and tubular body portion with one another so that an end portion of the first intestinal section, the support structure, and an end portion of the second intestinal section are disposed between the anvil member and the tubular body portion, the support structure being disposed between the first intestinal section and the second intestinal section; and firing the surgical anastomosis device to sever the portions of the first and second intestinal sections disposed radially inward of the annular knife, and to touch the portions of the first and second intestinal sections radially outward of the annular knife against the support structure.

The anvil assembly may include a first shaft and the tubular body portion may include a second shaft disposed radially inward of the annular knife. The first shaft of the anvil member may be attachable to the second shaft of the tubular body portion. The method may further include the step of attaching the first shaft of the anvil assembly to the second shaft of the tubular body portion prior to the step of approximating the anvil assembly to the tubular body portion.

The support structure may include an aperture formed therein. Accordingly, the method may further include the step of inserting one of the first shaft of the anvil assembly and the second shaft of the tubular body portion into the aperture of the support structure prior to the step of attaching the first shaft of the anvil assembly to the second shaft of the tubular body portion.

The tubular body portion may carry a plurality of surgical staples in a circular configuration. The surgical staples are disposed radially outward of the annular knife. Accordingly, upon firing of the anastomosis device, the plurality of staples penetrate a first interstitial section, the support structure and then a second interstitial section.

Desirably, the step of firing the surgical anastomosis device includes driving the plurality of staples from the tubular body portion through the second intestinal section, through the support structure, through the first intestinal section, and against the anvil member.

The support structure includes a disk shaped body portion having an upper surface, a lower surface, an outer terminal edge, and an inner terminal edge defining an aperture therein, the body portion defining a central axis through the aperture; and a first and a second membrane extending radially outward from the outer terminal edge of the body portion. The inner terminal edge of the body portion of the support structure extends radially inward of an inner radial edge of a staple cartridge assembly of the stapling apparatus when the support structure is positioned on the first shaft of the anvil assembly of the surgical anastomosis device. The aperture of the body portion of the support structure is dimensioned to receive the first shaft of the anvil assembly.

Each of the first and second membranes of the support structure may be made from a polymeric film, preferably, polyethylene.

The support structure may have an undeployed condition wherein the first and second membranes thereof are rolled-up towards the body portion, and a deployed condition wherein the first membrane extends in a substantially distal direction from the body portion of the support structure and the second membrane extends in a substantially proximal direction from the body portion of the support structure.

Desirably, a rip-cord may be rolled-up into each of the first and second membranes of the support structure when the support structure is in the undeployed condition. Each rip-cord may include a free end extending from the rolled-up membranes when the support structure is in the undeployed condition.

The method may further include the step of pulling on each rip-cord to unroll the first and second membranes over the first and second intestinal sections. Each of the first and second membranes of the support structure extends approximately 2.0 cm when un-rolled. Each membrane of the support structure includes a first inner layer and a second outer layer. The second outer layer of each membrane of the support structure swells at a rate greater than the first inner layer.

The support structure has an undeployed condition wherein the first and the second membranes extend substantially radially outward from the body portion thereof, and a deployed condition wherein the first membrane extends in a substantially distal direction from the body portion thereof and the second membrane extends in a substantially proximal direction from the body portion thereof. Accordingly, when the support structure is in the undeployed condition, the second outer layers of the first and second membranes are in juxtaposed relation to one another.

The second outer layers of the first and second membranes are made from a hydrogel. The first inner layer of each of the first and second membranes of the support structure is constructed from a substantially non-absorbable material. The first inner layer of each of the first and second membranes is fabricated from a bio-absorbable mesh fabric.

The support structure is positioned on the first shaft of the anvil assembly and the anvil assembly is approximated toward the staple cartridge assembly, the support structure is disposed between adjacent tissue sections to be anastomosed.

Desirably, when the support structure is disposed between the adjacent tissue sections, as second inner layers of first and second membranes absorb moisture, the first and second membranes curl in the direction of the first inner layer of respective first and second membranes such that the first outer layer contacts a respective intestinal section.

The first and second membranes of the support structure desirably extend approximately 2.0 cm from the outer terminal edge of the body portion of the support structure.

According to yet another aspect of the present disclosure, an anvil assembly for use with and operatively connectable to an annular surgical stapling device is provided. The anvil assembly includes an anvil member; a shaft extending from the anvil member; and a support structure assembly operatively supported on the shaft. The support structure assembly includes a sleeve defining a chamber therein, the sleeve being movable along the length of the shaft; and a support structure. The support structure includes a hub operatively supported on the shaft; a plurality of spokes extending from the hub; a disc supported on the spokes; and wound treatment material associated with the disc.

The sleeve is axially movable along the length of the shaft from a first position in which the support structure is in a collapsed condition and contained in the chamber of the sleeve and a second position in which the support structure is in an expanded condition and free from the sleeve.

The spokes are fabricated from a shape memory material. The disc is fabricated from a mesh. The disc is bio-absorbable. The reinforcing member may further include a ring connected to the spokes. The ring is fabricated from a shape memory material.

The wound treatment material is at least one of an adhesive, a sealant, a hemostat and a medicament. The adhesive is at least one of a protein derived, aldehyde-based adhesive material, and a cyanoacrylate-based material. The sealant is at least one of a fibrin sealant, a collagen-based and synthetic polymer-based tissue sealant, a synthetic polyethylene glycol-based sealant, and a hydrogel material. The hemostat material is at least one of a fibrin-based, a collagen-based, an oxidized regenerated cellulose-based and a gelatin-based topical hemostat, and fibrinogen-thrombin combination materials. The medicament is at least one of a drug, an enzyme, a growth factor, a peptide, a protein, a dye, a diagnostic agent and a hemostasis agent.

The sleeve may include a cam surface formed therein and the shaft includes a cam follower provided thereon, wherein the cam follower is configured to ride in the cam surface.

It is further contemplated that each of the structures described herein may be used with an annular surgical anastomosing device, not including any staples for securing tissue together, which is capable of approximating, adhering and cutting tissue.

Thus, it should be understood that various changes in form, detail and application of the structures of the present disclosure may be made without departing from the spirit and scope of the present disclosure.

What is claimed is:

1. A surgical stapling device for joining tissue portions, comprising:
    a handle assembly;
    an anvil assembly at a distal end of the stapling device, the anvil assembly having a shaft for removably connecting the anvil assembly to the stapling device;
    a tubular body portion, the tubular body portion having a staple cartridge assembly containing a plurality of surgical staples in an annular array, the anvil assembly and tubular body portion being juxtaposed with respect to one another along the shaft and arranged so as to be approximated with respect to one another; and
    an applicator supported on the shaft of the anvil assembly, the applicator having a disc-shaped structure disposed between the anvil member and tubular body portion, the disc-shaped structure having a channel radially oriented and open at lateral sides of the disc-shaped structure, the channel being arranged for dispensing a wound treatment material.

2. The surgical stapling device according to claim 1, wherein the handle assembly includes a grip that is used to approximate the anvil assembly and tubular body portion.

3. The surgical stapling device according to claim 1, wherein the disc-shaped structure is substantially rigid.

4. The surgical stapling device according to claim 1, wherein the wound treatment material is at least one of an adhesive, a sealant, a hemostat, and a medicament.

5. The surgical stapling device according to claim 1, wherein the applicator includes a sleeve operatively connected to the anvil assembly.

6. The surgical stapling device according to claim 5, wherein the channel is in fluid communication with the sleeve.

7. The surgical stapling device according to claim 6, wherein the wound treatment material is retained within and dispensed from the sleeve.

8. The surgical stapling device according to claim 7, wherein the channel is in fluid communication with the sleeve.

9. The surgical stapling device according to claim 5, wherein the applicator includes an ampoule selectively positionable within the sleeve, wherein the wound treatment material is retained within and dispensed from the ampoule.

10. The surgical stapling device according to claim 9, wherein the shaft and the sleeve form a plunger for compressing the amouple and dispensing the wound treatment material.

11. The surgical stapling device according to claim 5, wherein the sleeve includes a portion through which the interior of the tubular sleeve is visible.

12. The surgical stapling device according to claim 11, wherein the sleeve selectively engages a connection member of the surgical stapling device.

13. The surgical stapling device according to claim 5, wherein the disc-shaped structure is supported on the distal end of the sleeve.

14. The surgical stapling device according to claim 1, wherein the disc-shaped structure includes a manifold supported on the anvil assembly, wherein the manifold defines the channels therein for directing a flow of wound treatment material onto an interface between the tissue portions.

15. The surgical stapling device according to claim 1, wherein the applicator includes a seal.

16. The surgical stapling device according to claim 1, further comprising an annular knife disposed radially inwardly of the staples.

* * * * *